(12) United States Patent
Fleischman et al.

(10) Patent No.: US 6,939,349 B2
(45) Date of Patent: Sep. 6, 2005

(54) STRUCTURES FOR DEPLOYING ELECTRODE ELEMENTS

(75) Inventors: Sidney D. Fleischman, Durham, NC (US); Thomas M. Bourne, Mountain View, CA (US); James G. Whayne, Chapel Hill, NC (US); David K. Swanson, Campbell, CA (US)

(73) Assignee: EP Technologies, Inc., San Jose, CA (US)

( * ) Notice: Subject to any disclaimer, the term of this patent is extended or adjusted under 35 U.S.C. 154(b) by 0 days.

(21) Appl. No.: 10/875,097

(22) Filed: Jun. 22, 2004

(65) Prior Publication Data

US 2005/0049585 A1 Mar. 3, 2005

(Under 37 CFR 1.47)

Related U.S. Application Data

(63) Continuation of application No. 10/370,334, filed on Feb. 18, 2003, now Pat. No. 6,893,439, which is a continuation of application No. 09/795,627, filed on Feb. 28, 2001, now Pat. No. 6,544,262, which is a continuation of application No. 09/524,080, filed on Mar. 13, 2000, now Pat. No. 6,214,002, which is a continuation of application No. 09/205,058, filed on Dec. 3, 1998, now Pat. No. 6,071,282, which is a continuation of application No. 08/321,424, filed on Oct. 11, 1994, now Pat. No. 5,885,278, which is a continuation-in-part of application No. 08/320,198, filed on Oct. 7, 1994, now abandoned.

(51) Int. Cl.$^7$ .......................... A61B 18/14; A61B 5/408; A61N 1/05
(52) U.S. Cl. .......................... 606/41; 600/374; 607/122
(58) Field of Search .................................. 600/374, 381; 606/41, 45, 47, 49; 607/122, 126

(56) References Cited

U.S. PATENT DOCUMENTS

| 4,181,131 A | 1/1980 | Ogiu |
| 4,294,254 A | 10/1981 | Chamness |

(Continued)

FOREIGN PATENT DOCUMENTS

| EP | 0 238 106 A1 | 9/1987 |
| GB | 2 032 278 A | 10/1978 |

*Primary Examiner*—Lee S. Cohen
(74) *Attorney, Agent, or Firm*—Henricks, Slavin & Holmes LLP

(57) ABSTRACT

An electrode support structure comprises a guide body having at its distal end a flexible spline leg. The spline leg is flexed to define an arcuate shape to facilitate intimate contact against tissue. An electrode element is carried by the spline leg for movement along its axis. The structure includes a control element coupled to the electrode element. The control element remotely imparts force to move the electrode element along the axis of the spline leg. Therefore, in use, the physician can cause the electrode element to travel along a path that the spline leg defines, without otherwise changing the location of the guide body.

28 Claims, 27 Drawing Sheets

U.S. PATENT DOCUMENTS

| | | | |
|---|---|---|---|
| 4,294,256 A | 10/1981 | Greatbatch | |
| 4,493,320 A | 1/1985 | Treat | |
| 4,522,212 A | 6/1985 | Gelinas | |
| 4,532,924 A | 8/1985 | Auth et al. | |
| 4,660,571 A | 4/1987 | Hess et al. | |
| 4,699,147 A | 10/1987 | Chilson et al. | |
| 4,765,331 A | 8/1988 | Petruzzi et al. | |
| 5,125,928 A | 6/1992 | Parins et al. | |
| 5,150,717 A | 9/1992 | Rosen et al. | |
| 5,156,151 A | 10/1992 | Imran | |
| 5,263,493 A | 11/1993 | Avitall | |
| 5,313,943 A | 5/1994 | Houser et al. | |
| 5,318,564 A | 6/1994 | Eggers et al. | |
| 5,324,284 A | 6/1994 | Imran | |
| 5,327,905 A | 7/1994 | Avitall | |
| 5,345,936 A | 9/1994 | Pomeranz et al. | |
| 5,366,443 A | 11/1994 | Eggers et al. | |
| 5,370,675 A | 12/1994 | Edwards et al. | |
| 5,387,219 A | 2/1995 | Rappe | |
| 5,397,342 A | 3/1995 | Heil, Jr. et al. | |
| 5,406,946 A | 4/1995 | Imran | |
| 5,411,025 A | 5/1995 | Webster, Jr. | |
| 5,437,665 A | 8/1995 | Munro | |
| 5,454,370 A | 10/1995 | Avitall | |
| 5,482,037 A | 1/1996 | Borghi | |
| 5,487,385 A | 1/1996 | Avitall | |
| 5,575,810 A | 11/1996 | Swanson | |
| 5,582,609 A | 12/1996 | Swanson et al. | |
| 5,617,854 A | 4/1997 | Munsif | |
| 5,626,136 A | 5/1997 | Webster, Jr. | |
| 5,673,695 A | 10/1997 | McGee et al. | |
| 5,702,368 A | 12/1997 | Stevens et al. | |
| 5,738,683 A | 4/1998 | Osypka | |
| 5,836,947 A | 11/1998 | Fleischman | |
| 5,885,278 A | 3/1999 | Fleischman | |
| 6,012,457 A | 1/2000 | Lesh | |
| 6,024,740 A | 2/2000 | Lesh et al. | |
| 6,071,282 A | 6/2000 | Fleischman | |
| 6,117,101 A | 9/2000 | Diederich et al. | |
| 6,142,994 A | 11/2000 | Swanson et al. | |
| 6,164,283 A | 12/2000 | Lesh | |
| 6,214,002 B1 | 4/2001 | Fleischman | |
| 6,241,754 B1 | 6/2001 | Swanson et al. | |
| 6,245,064 B1 | 6/2001 | Lesh et al. | |
| 6,254,599 B1 | 7/2001 | Lesh et al. | |
| 6,425,895 B1 | 7/2002 | Swanson et al. | |
| 6,544,262 B2 | 4/2003 | Fleischman | |

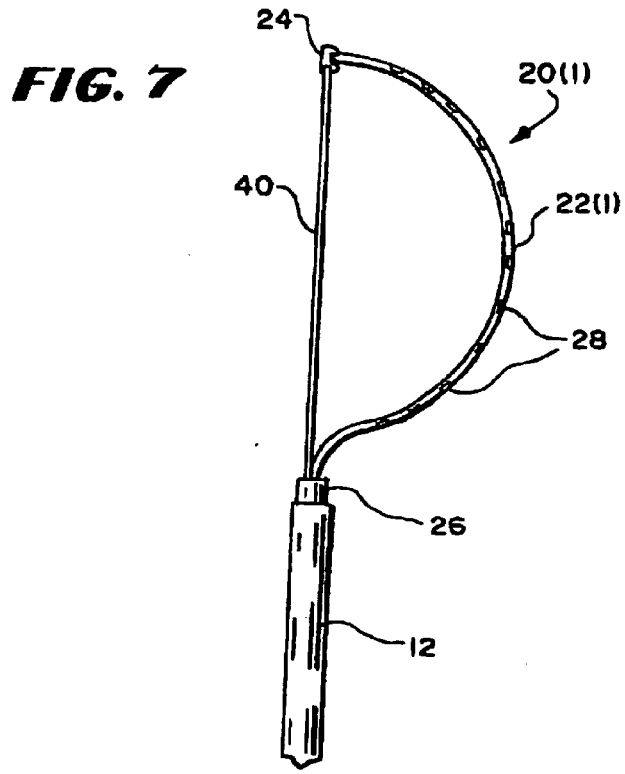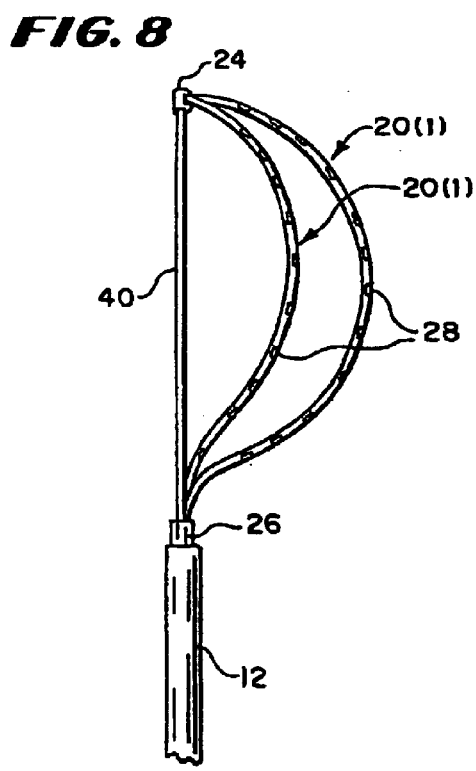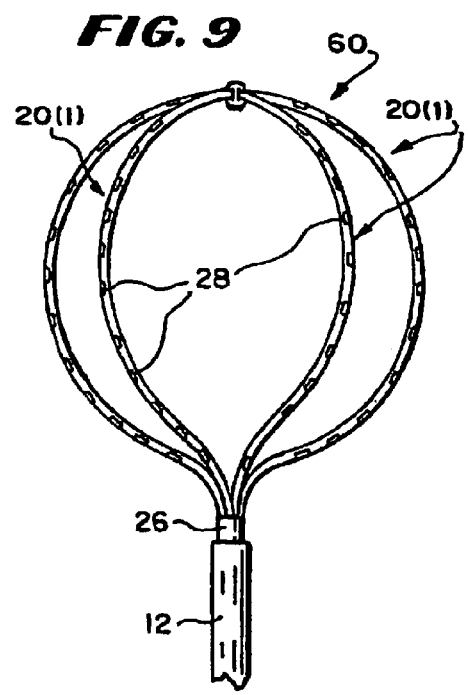

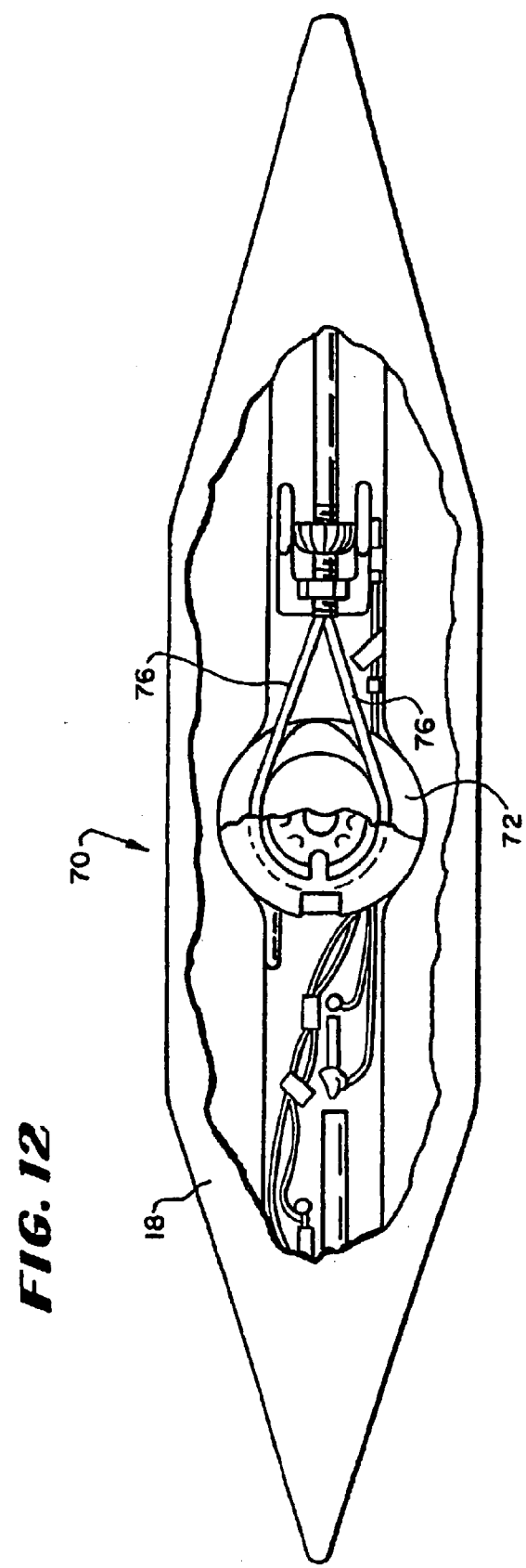

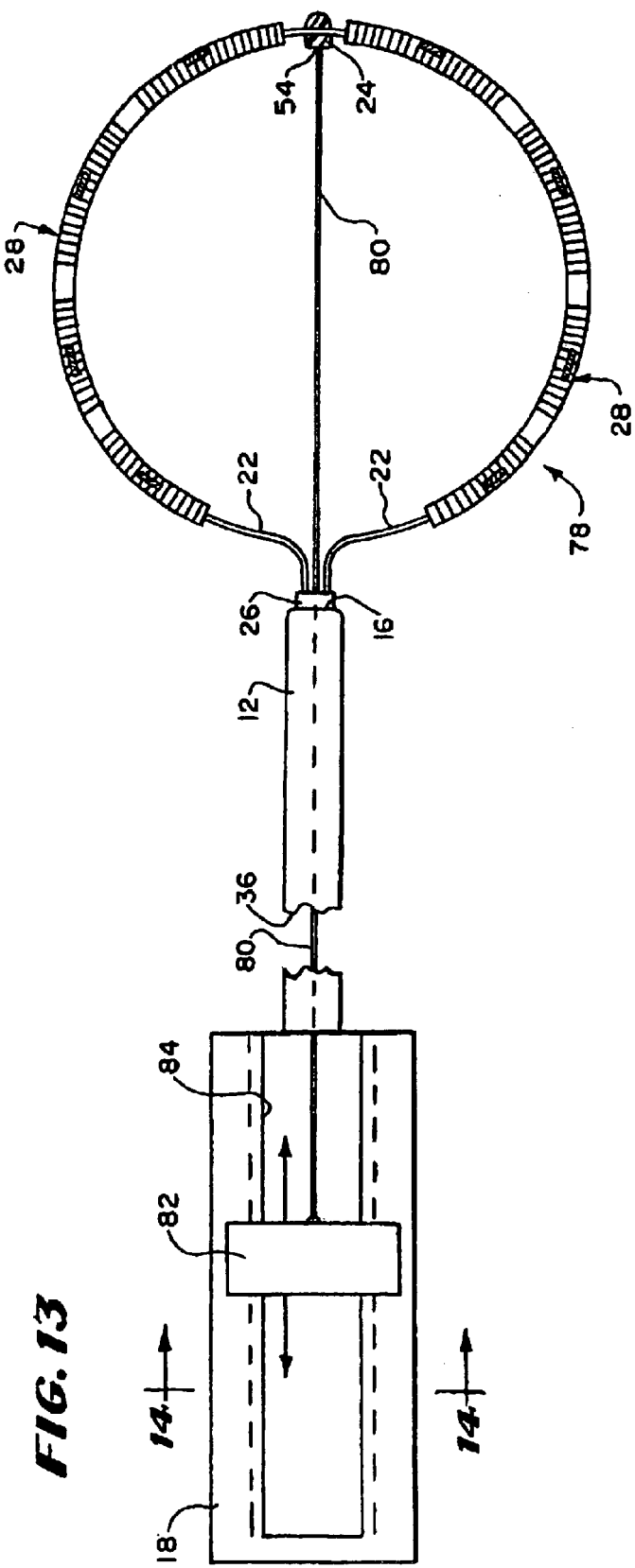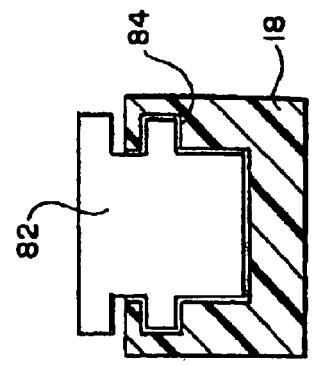

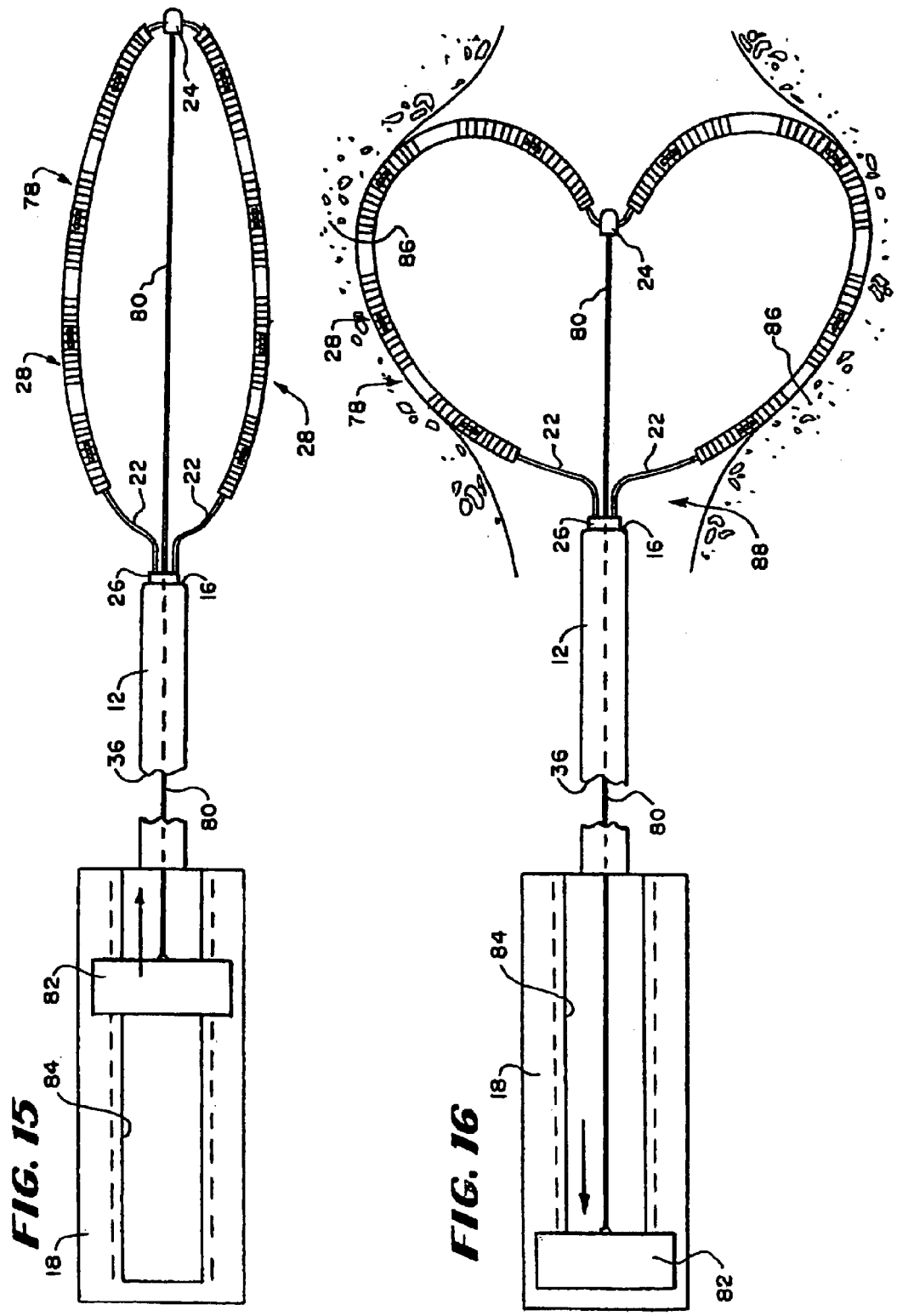

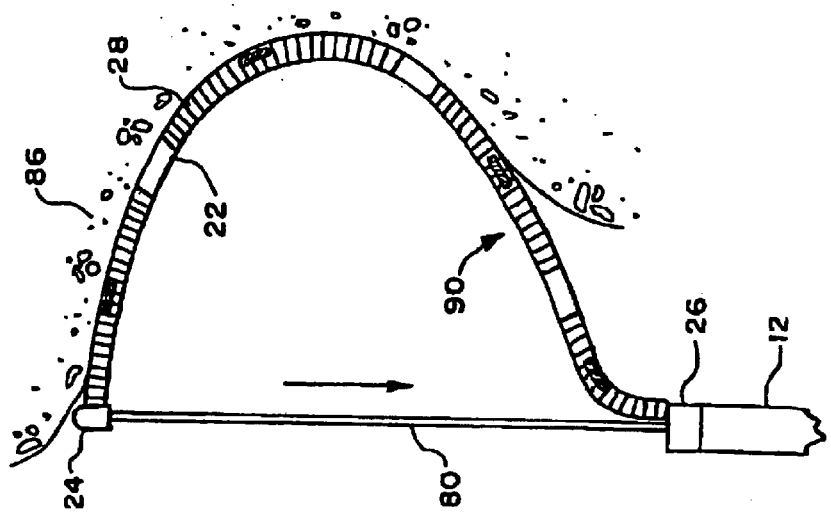
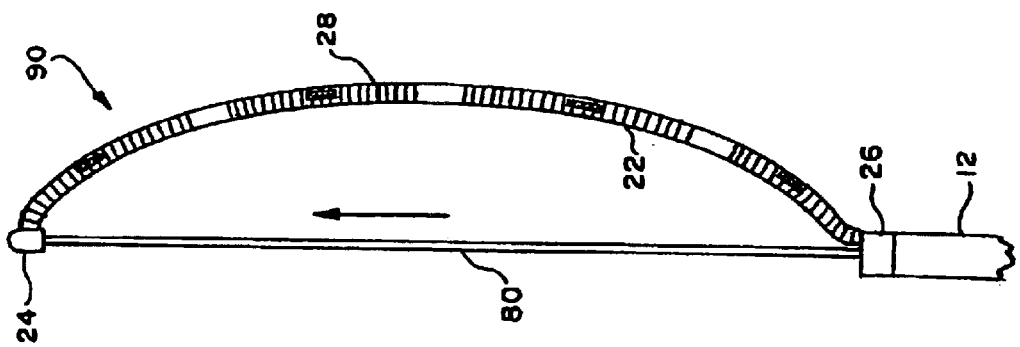
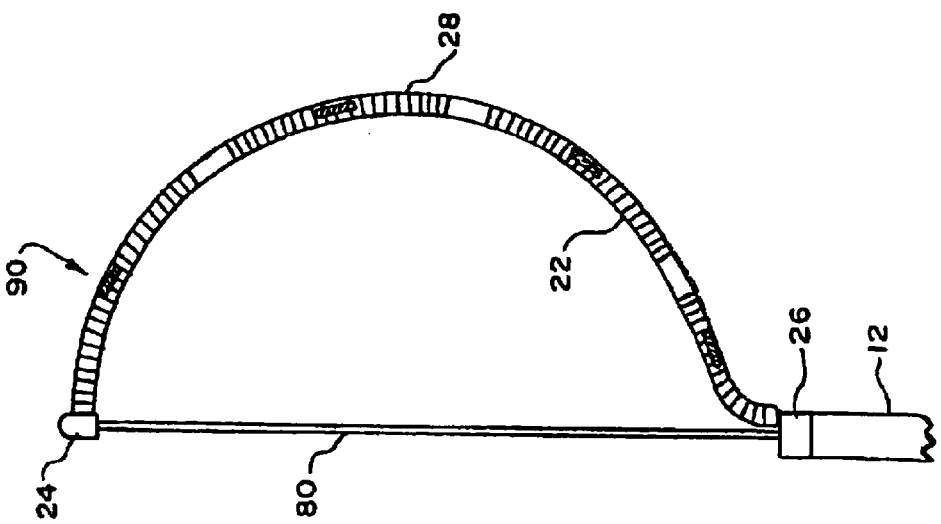

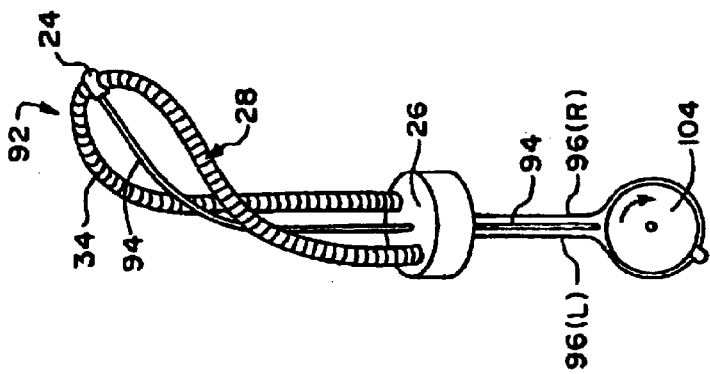
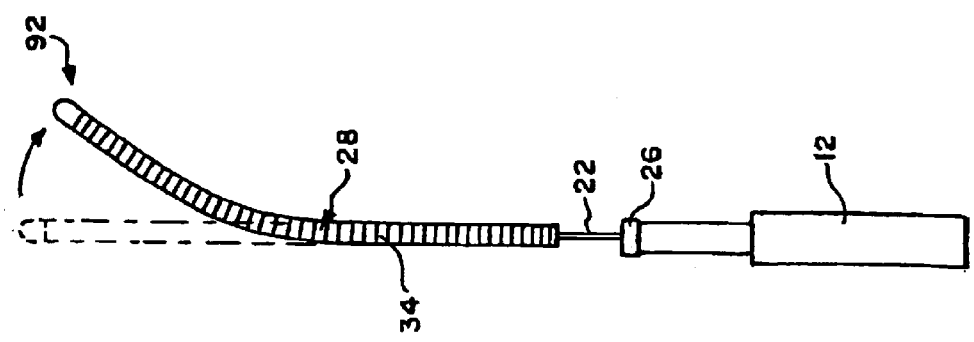
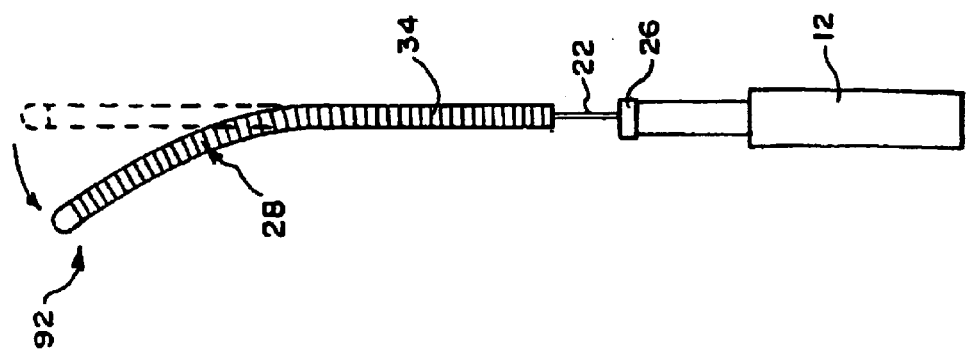

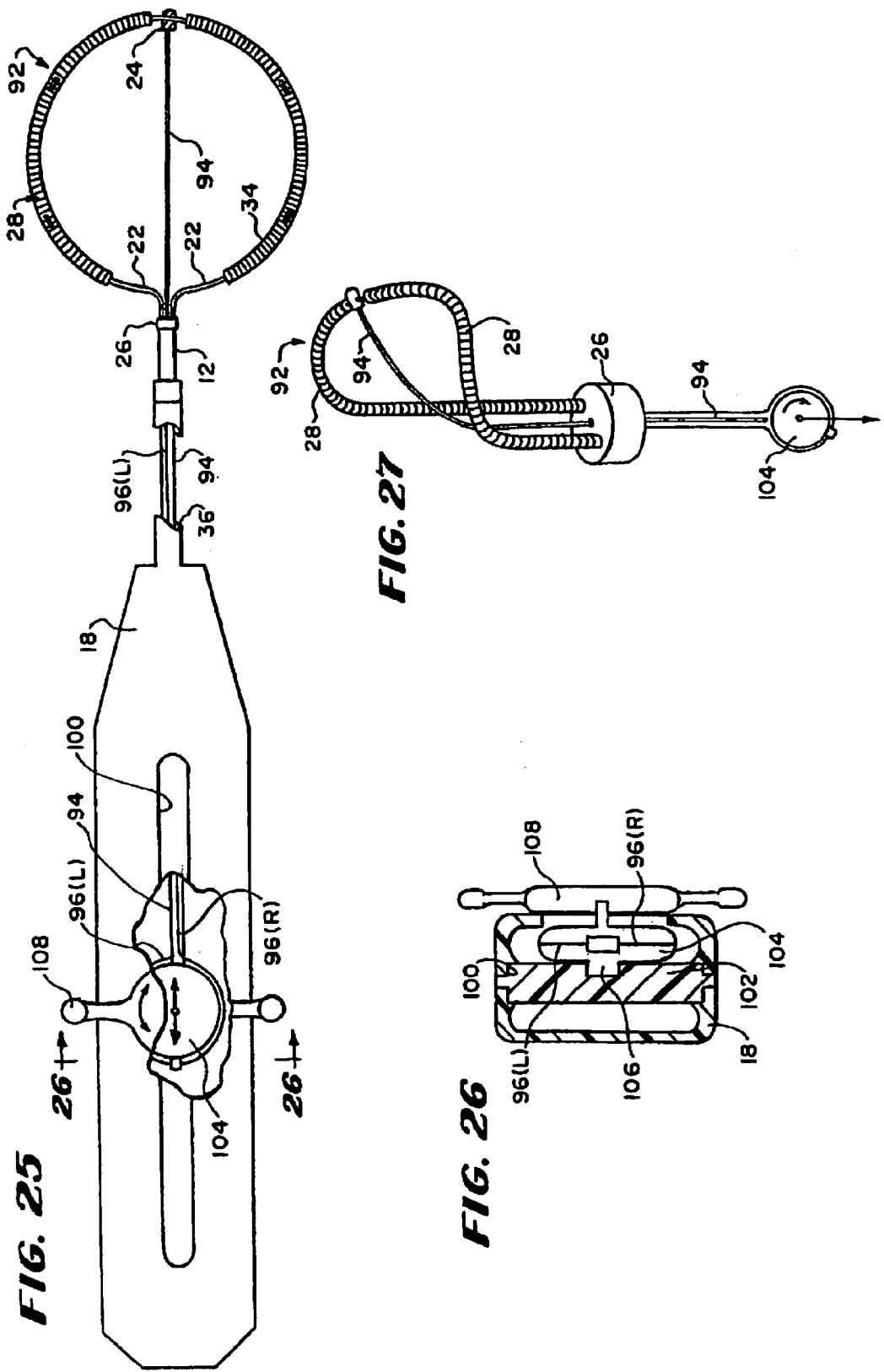

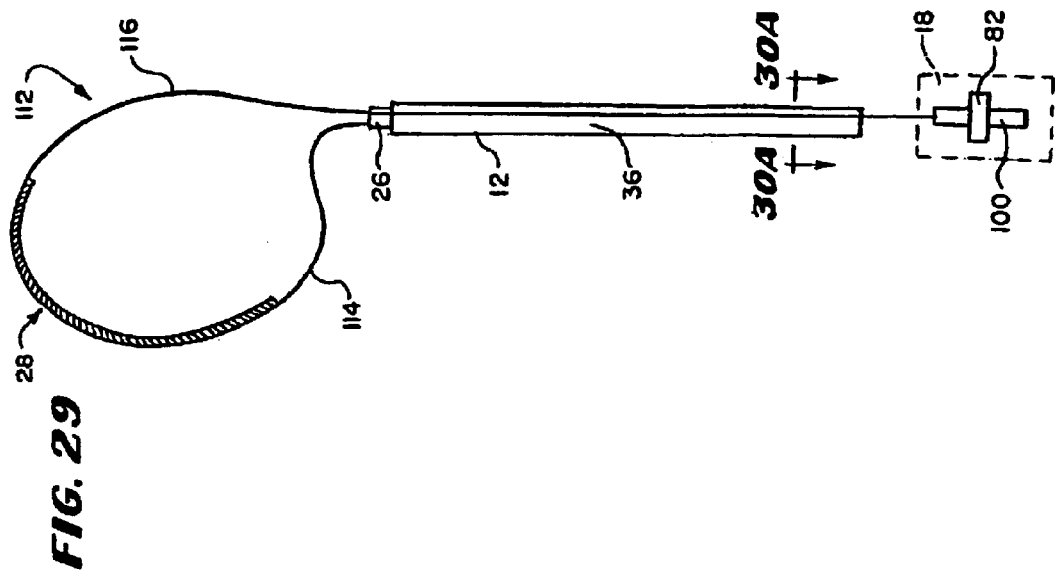
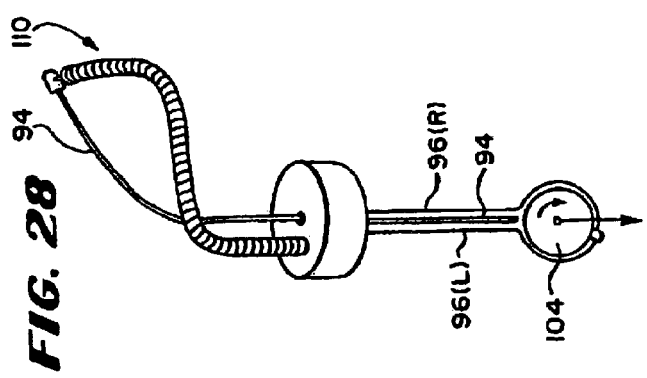

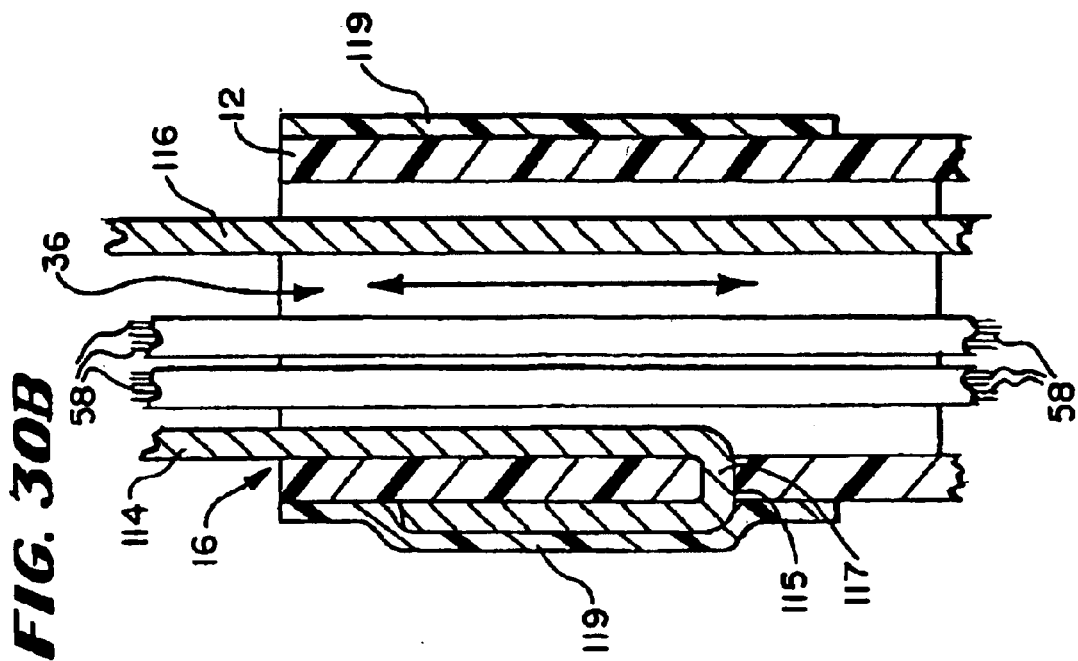
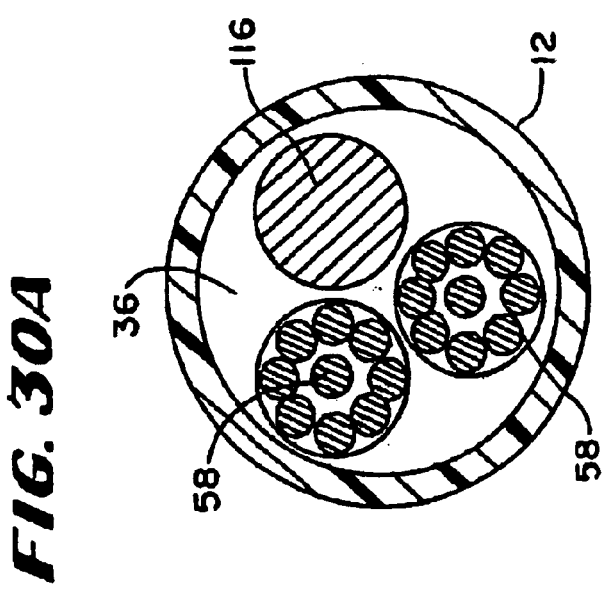

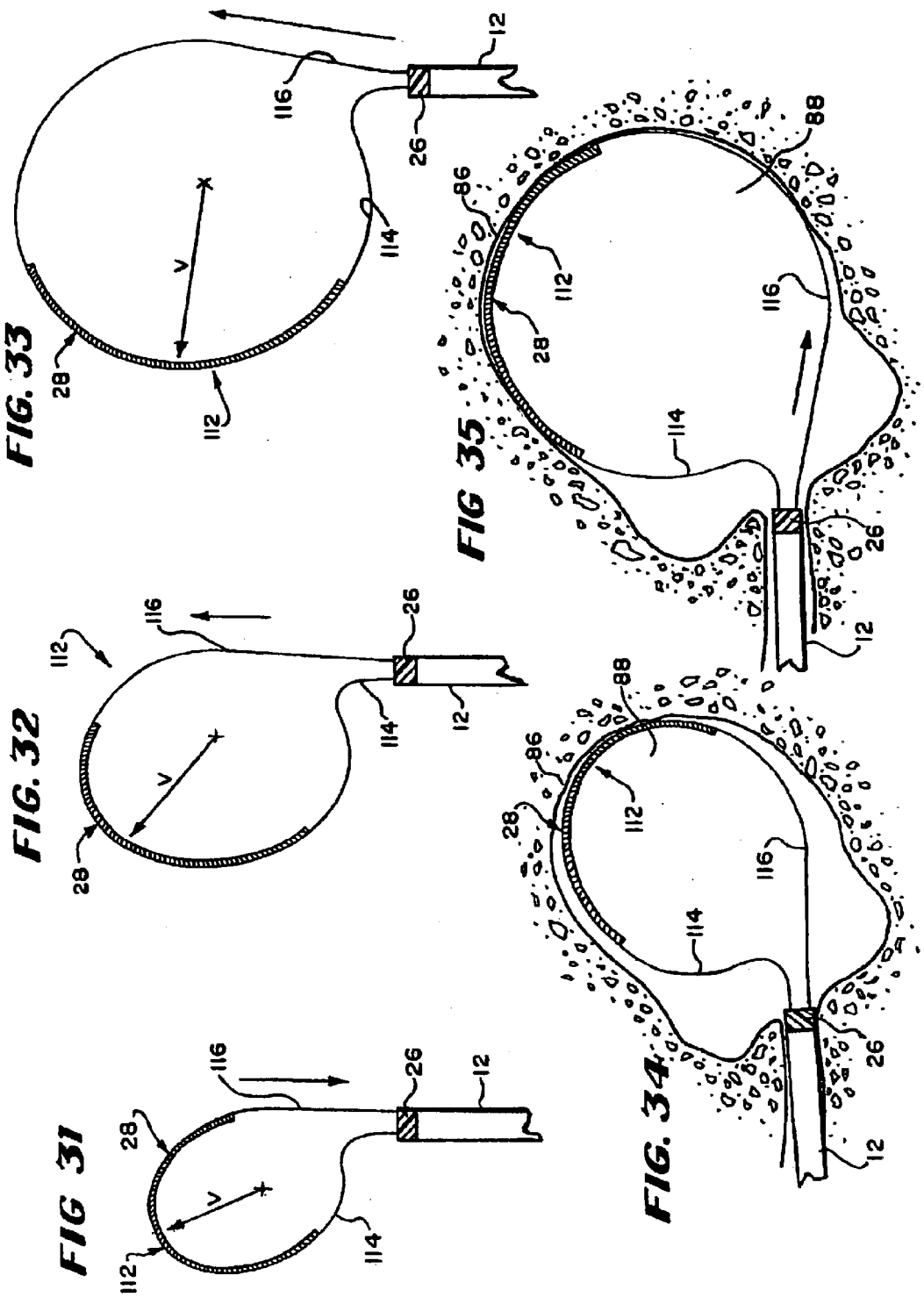

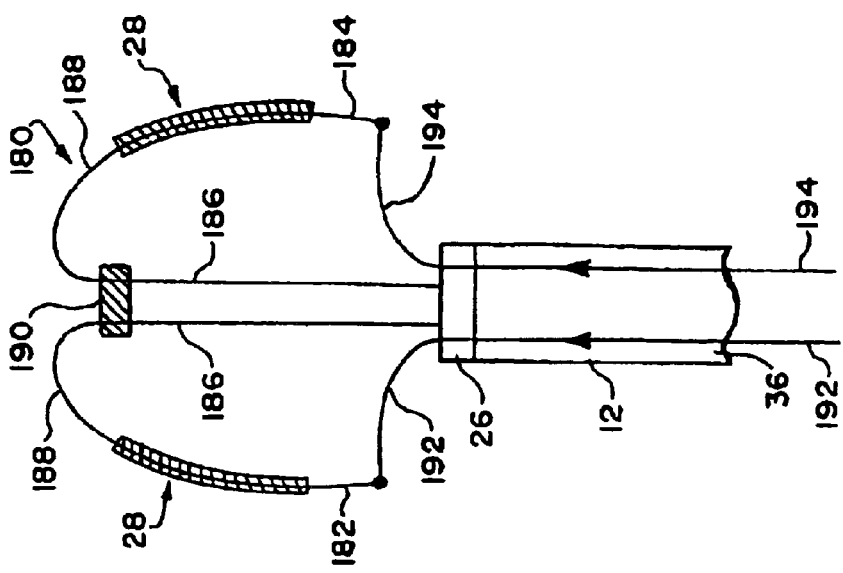
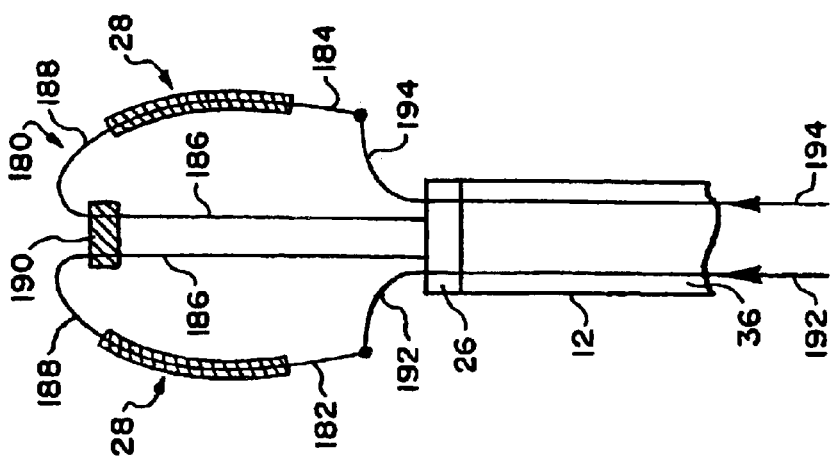
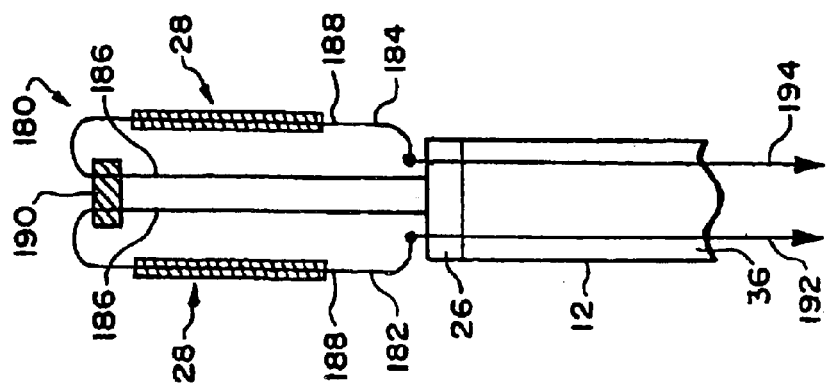

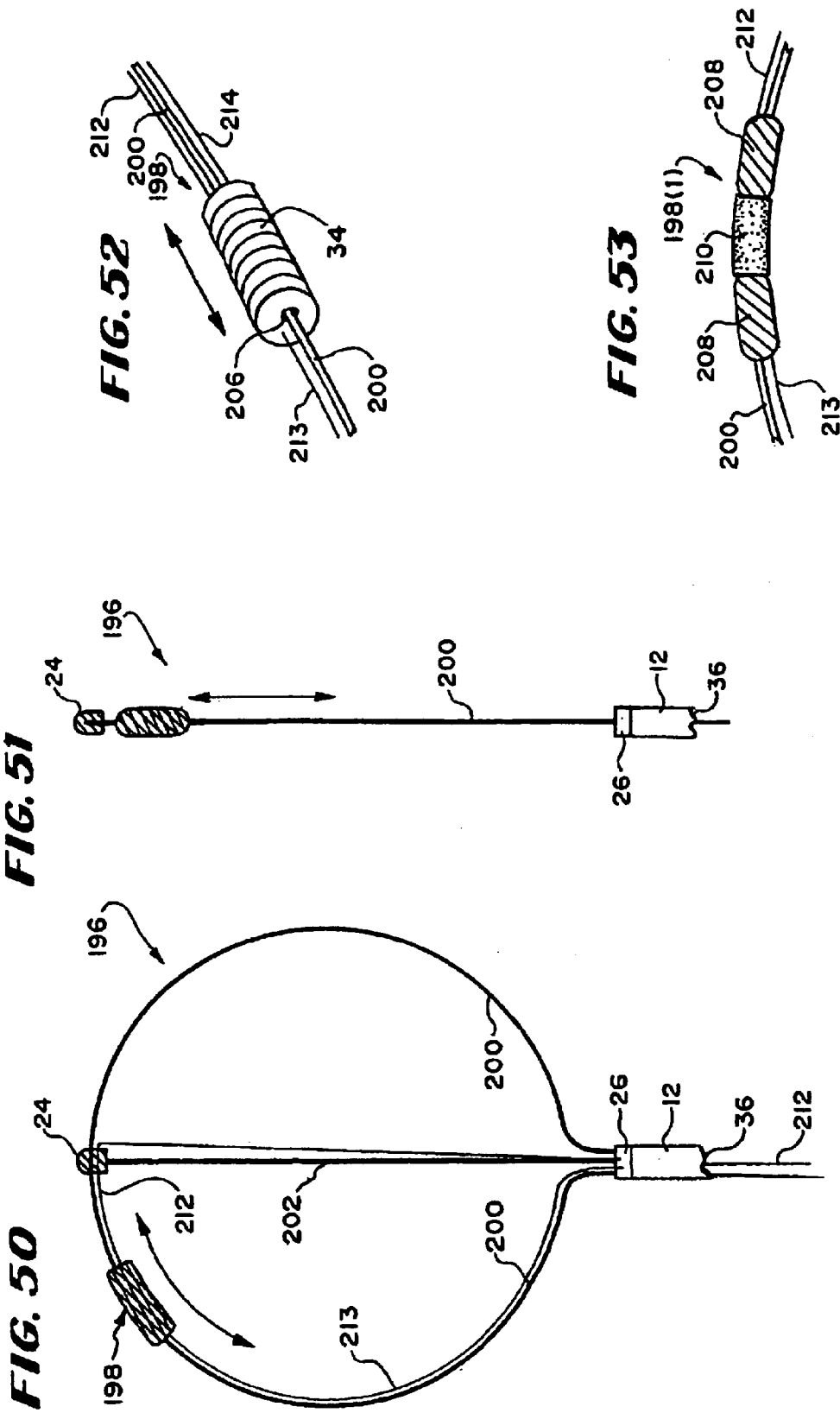

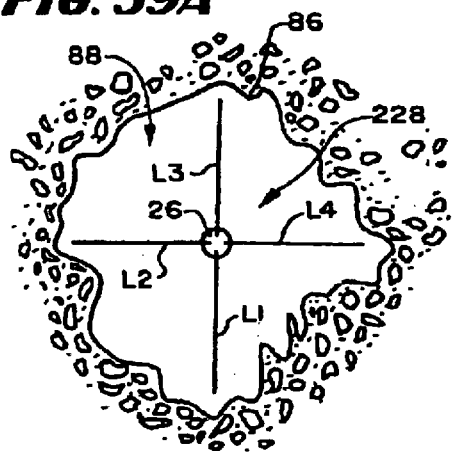
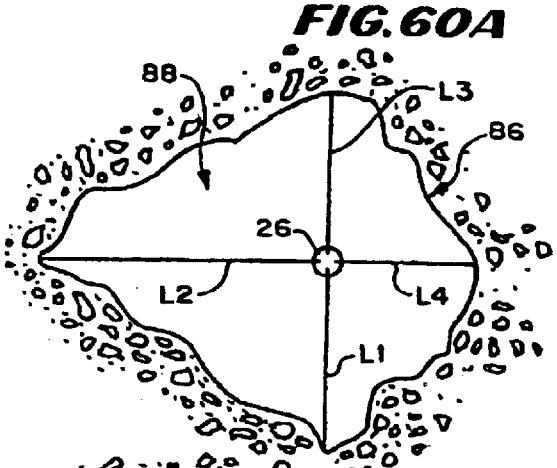
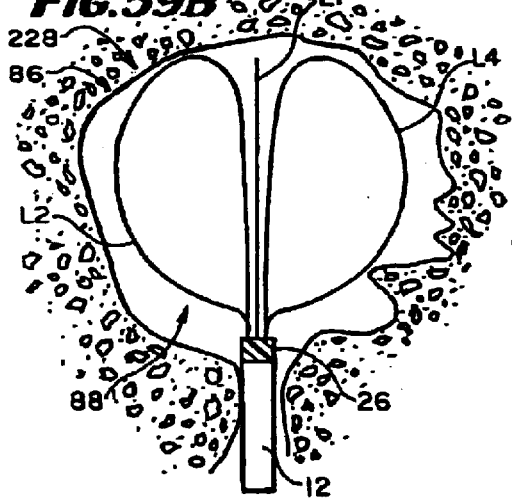
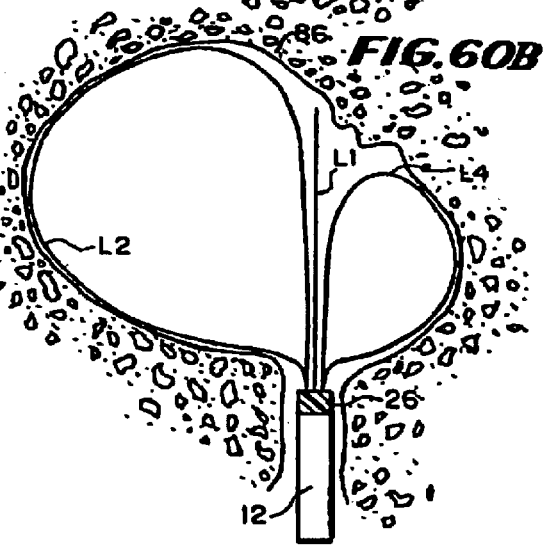

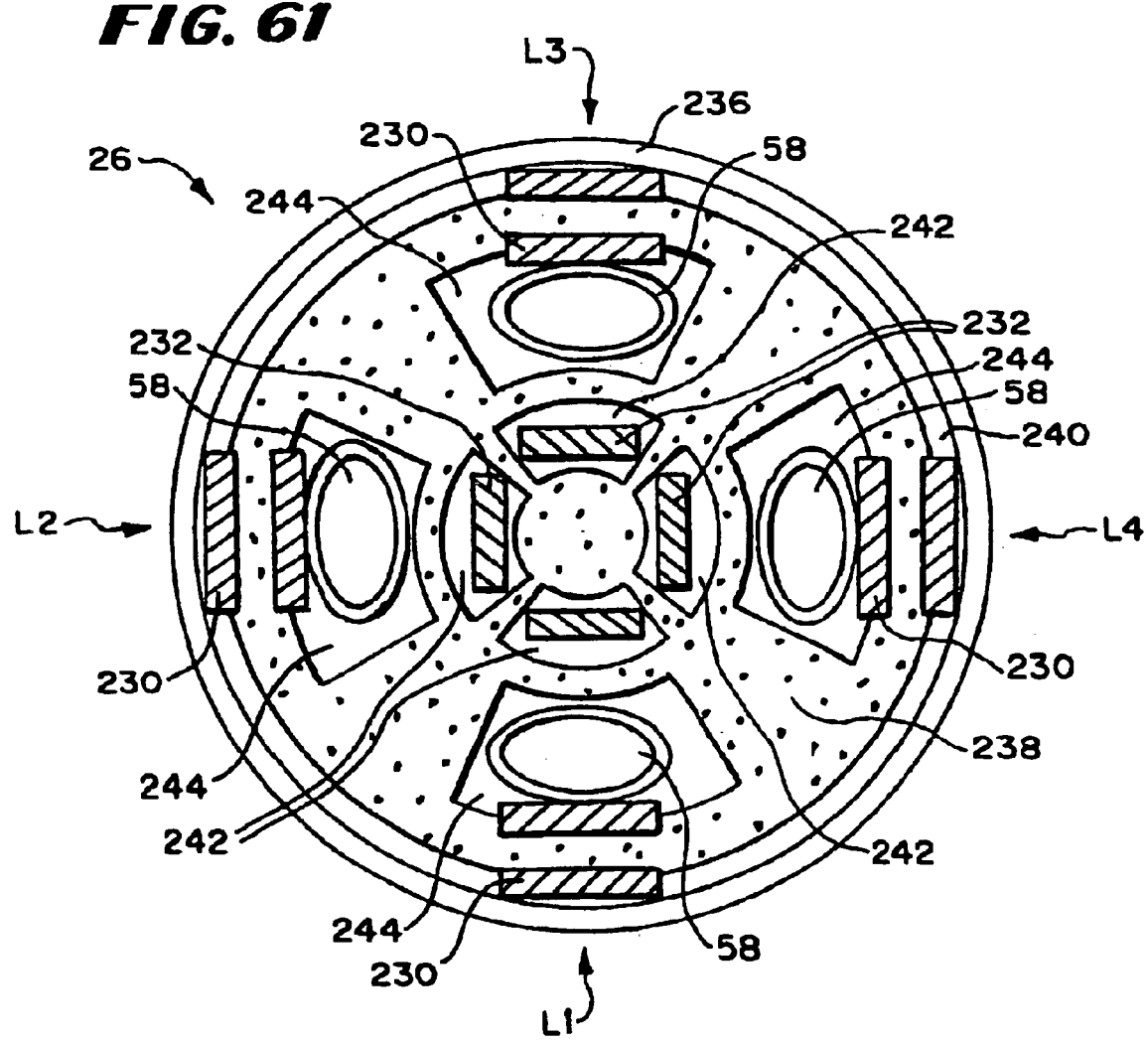

STRUCTURES FOR DEPLOYING ELECTRODE ELEMENTS

CROSS-REFERENCE TO RELATED APPLICATIONS

This application is a continuation of application Ser. No. 10/370,334, filed Feb. 18, 2003, now U.S. Pat. No. 6,893,439, which is a continuation of application Ser. No. 09/795,627, filed Feb. 28, 2001, now U.S. Pat. No. 6,544,262, which is a continuation of application Ser. No. 09/524,080, filed Mar. 13, 2000, now U.S. Pat. No. 6,214,002, which is a continuation of application Ser. No. 09/205,058, filed Dec. 3, 1998, now U.S. Pat. No. 6,071,282, which is a continuation of application Ser. No. 08/321,424, filed Oct. 11, 1994, now U.S. Pat. No. 5,885,278, which is a continuation in part of application Ser. No. 08/320,198, filed Oct. 7, 1994, now abandoned.

FIELD OF THE INVENTION

The invention relates to systems and methods for ablating myocardial tissue for the treatment of cardiac conditions.

BACKGROUND OF THE INVENTION

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract.

The AV node regulates the propagation delay to the atrioventricular bundle (or "HIS" bundle). This coordination of the electrical activity of the heart causes atrial systole during ventricular diastole. This, in turn, improves the mechanical function of the heart.

Today, as many as 3 million Americans experience atrial fibrillation and atrial flutter. These people experience an unpleasant, irregular heart beat, called arrhythmia. Because of a loss of atrioventricular synchrony, these people also suffer the consequences of impaired hemodynamics and loss of cardiac efficiency. They are more at risk of stroke and other thromboembolic complications because of loss of effective contraction and atrial stasis.

Treatment is available for atrial fibrillation and atrial flutter. Still, the treatment is far from perfect.

For example, certain antiarrhythmic drugs, like quinidine and procainamide, can reduce both the incidence and the duration of atrial fibrillation episodes. Yet, these drugs often fail to maintain sinus rhythm in the patient.

Cardioactive drugs, like digitalis, Beta blockers, and calcium channel blockers, can also be given to control the ventricular response. However, many people are intolerant to such drugs.

Anticoagulant therapy also combats thromboembolic complications.

Still, these pharmacologic remedies often do not remedy the subjective symptoms associated with an irregular heartbeat. They also do not restore cardiac hemodynamics to normal and remove the risk of thromboembolism.

Many believe that the only way to really treat all three detrimental results of atrial fibrillation and flutter is to actively interrupt all the potential pathways for atrial reentry circuits.

James L. Cox, M.D. and his colleagues at Washington University (St. Louis, Mo.) have pioneered an open heart surgical procedure for treating atrial fibrillation, called the "maze procedure." The procedure makes a prescribed pattern of incisions to anatomically create a convoluted path, or maze, for electrical propagation within the left and right atria, therefore its name. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits.

The maze procedure has been found very effective in curing atrial fibrillation. Yet, despite its considerable clinical success, the maze procedure is technically difficult to do. It requires open heart surgery and is very expensive. Because of these factors, only a few maze procedures are done each year.

It is believed the treatment of atrial fibrillation and flutter requires the formation of long, thin lesions of different lengths and curvilinear shapes in heart tissue. Such long, thin lesion patterns require the deployment within the heart of flexible ablating elements having multiple ablating regions. The formation of these lesions by ablation can provide the same therapeutic benefits that the complex incision patterns that the surgical maze procedure presently provides, but without invasive, open heart surgery.

With larger and/or longer multiple electrode elements comes the demand for more precise control of the ablating process. The delivery of ablating energy must be governed to avoid incidences of tissue damage and coagulum formation. The delivery of ablating energy must also be carefully controlled to assure the formation of uniform and continuous lesions, without hot spots and gaps forming in the ablated tissue.

The task is made more difficult because heart chambers vary in size from individual to individual. They also vary according to the condition of the patient. One common effect of heart disease is the enlargement of the heart chambers. For example, in a heart experiencing atrial fibrillation, the size of the atrium can be up to three times that of a normal atrium.

One objective of the invention is to provide tissue ablation systems and methods providing beneficial therapeutic results without requiring invasive surgical procedures.

Another objective of the invention is to provide systems and methods that simplify the creation of complex lesions patterns in body tissue, such as in the heart.

SUMMARY OF THE INVENTION

A principal objective of the invention is to provide improved structures and methodologies for deploying electrode elements in contact with tissue. In a preferred implementation, the structures and methodologies that embody features of the invention make possible the creation of long, thin lesion patterns in tissue for the treatment of, for example, heart conditions like atrial fibrillation or atrial flutter.

In achieving these objectives, the invention provides an electrode support structure comprising a guide body having at its distal end a flexible spline leg. The spline leg is flexed to define an arcuate shape to facilitate intimate contact against tissue. An electrode element is carried by the spline leg for movement along its axis. The structure includes a control element coupled to the electrode element. The control element remotely imparts force to move the electrode element along the axis of the spline leg. Therefore, in use, the physician can cause the electrode element to travel along a path that the spline leg defines, without otherwise changing the location of the guide body.

The invention also provides a method for ablating tissue in a heart. The method introduces a probe into the heart. The probe carries at least one elongated spline leg flexed outward of the probe to define an arcuate shape. The probe also includes at least one ablation electrode that is movable along the at least one spline leg spline in response to the application of force. The method establishes contact between the ablation electrode and a region of heart tissue, along which the spline leg defines an elongated path. The method transmits ablation energy to the ablation electrode while in contact with the tissue region. The method also applies force to move the ablation electrode along the at least one spline leg, while maintaining contact with the tissue, to ablate tissue along the elongated path.

Other features and advantages of the inventions are set forth in the following Description and Drawings, as well as in the appended Claims.

BRIEF DESCRIPTION OF THE DRAWINGS

FIG. 7 is an elevation view of a half-loop structure for supporting multiple electrodes;

FIG. 8 is an elevation view of a composite loop structure for supporting multiple electrodes comprising two circumferentially spaced half-loop structures;

FIG. 9 is an elevation view of a composite loop structure comprising two full-loop structures positioned ninety degrees apart;

FIG. 12 is a top view of a steering mechanism used to deflect the distal end of the probe shown in FIG. 1;

FIG. 13 is a plan view of a full-loop structure for supporting multiple electrode elements having an associated center stylet attached to a remote control knob for movement to extend and distend the full-loop structure;

FIG. 14 is a side section view of the remote control knob for the center stylet shown in FIG. 13;

FIG. 15 is a plan view of the full-loop structure shown in FIG. 13, with the control knob moved to extend the full-loop structure;

FIG. 16 is a plan view of a full-loop structure shown in FIG. 13, with the control handle moves to distend the full-loop structure;

FIG. 17 is a plan view of a half-loop structure for supporting multiple electrode elements having an associated center stylet attached to a remote control knob for movement to extend and distend the half-loop structure;

FIG. 18 is a plan view of the half-loop structure shown in FIG. 17, with the control knob moved to extend the half-loop structure;

FIG. 19 is a plan view of a half-loop structure shown in FIG. 17, with the control handle moves to distend the half-loop structure;

FIGS. 23A and 23B are side elevation views showing the operation of the steering mechanism in bending the full-loop structure, respectively, to the left and to the right;

FIG. 24 is a largely diagrammatic, perspective view of the full-loop structure bent to the right, as also shown in side elevation in FIG. 23B;

FIG. 25 is a plan view of the full-loop structure shown in FIG. 20 and the associated remote control knob for extending and distending as well as bending the full-loop structure;

FIG. 26 is a side section view, taken generally along lines 26—26 in FIG. 25, of the control knob for extending and distending as well as bending the full-loop structure;

FIG. 27 is a largely diagrammatic, perspective view of the full-loop structure when distended and bent to the right;

FIG. 28 is a largely diagrammatic, perspective view of a half-loop structure with steerable center stylet bent to the right;

FIG. 29 is a plan, partially diagrammatic, view of a full-loop structure for supporting multiple electrode elements having a movable spline leg attached to a remote control knob for movement to extend and distend the full-loop structure;

FIG. 30A is a section view, taken generally along line 30A—30A in FIG. 29, of the interior of the catheter body lumen, through which the movable spline leg passes;

FIG. 30B is a side section view of an alternative way of securing the full-loop structure shown in FIG. 29 to the distal end of the catheter tube;

FIG. 31 is a plan, partially diagrammatic view of the full-loop structure shown in FIG. 29 being extended by pulling the movable spline leg inward;

FIGS. 32 and 33 are plan, partially diagrammatic views of the full-loop structure shown in FIG. 29 being distended by pushing the movable spline leg outward;

FIGS. 34 and 35 are largely diagrammatic views of the full-loop structure shown in FIG. 29 being distended by pushing the movable spline leg outward while deployed in the atrium of a heart;

FIGS. 47, 48, and 49 are plan, partially diagrammatic, views of another alternative form of a bifurcated full-loop structure for supporting multiple electrode elements having movable half-loop structures to extend and distend the bifurcated full-loop structure;

FIG. 50 is a plan view of a full-loop structure for supporting and guiding a movable electrode element;

FIG. 51 is a side elevation view of the full-loop structure and movable electrode element shown in FIG. 50;

FIG. 52 is an enlarged view of the movable electrode supported and guided by the structure shown in FIG. 50, comprising wound coils wrapped about a core body;

FIG. 53 is an enlarged view of another movable electrode that can be supported and guided by the structure shown in FIG. 50, comprising bipolar pairs of electrodes;

FIGS. 59A and 59B are, respectively, top and side views of a bundled loop structure like that shown in FIG. 55 in position within an atrium, out of contact with the surrounding atrial wall;

FIGS. 60A and 60B are, respectively, top and side views of a bundled loop structure like that shown in FIG. 57, with some of the independently movable spline legs extended and distended to change the flexure of the bundled loop structure, to bring it into contact with the surrounding atrial wall; and FIG. 61 is a top section view of the base of the bundled loop structure shown in FIG. 55.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

This Specification discloses multiple electrode structures that embody aspects the invention. This Specification also discloses tissue ablation systems and techniques using multiple temperature sensing elements that embody other aspects of the invention. The illustrated and preferred embodiments discuss these structures, systems, and techniques in the context of catheter-based cardiac ablation. That is because these structures, systems, and techniques are well suited for use in the field of cardiac ablation.

Still, it should be appreciated that the invention is applicable for use in other tissue ablation applications. For example, the various aspects of the invention have application in procedures for ablating tissue in the prostrate, brain, gall bladder, uterus, and other regions of the body, using systems that are not necessarily catheter-based.

I. Loop Support Structures for Multiple Electrodes

Figure 1:
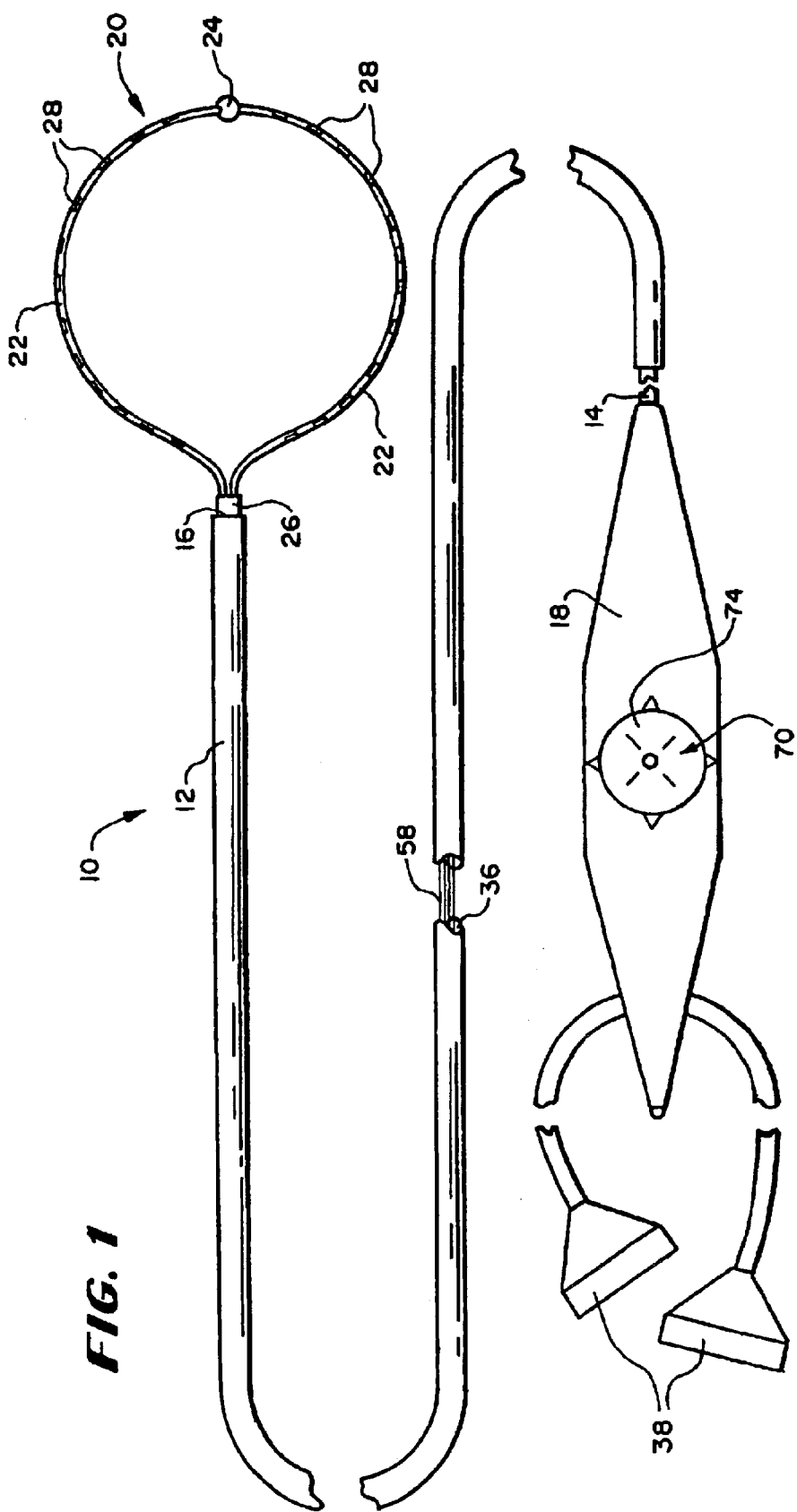
FIG. 1 is a plan view of an ablation probe having a full-loop structure for supporting multiple ablation elements.

FIG. 1 shows a multiple electrode probe 10 that includes a loop structure 20 carrying multiple electrode elements 28.

The probe 10 includes a flexible catheter tube 12 with a proximal end 14 and a distal end 16. The proximal end 14 carries an attached handle 18. The distal end 16 carries a loop structure 20 that supports multiple electrodes.

In FIG. 1, the loop support structure 20 comprises two flexible spline legs 22 spaced diametrically opposite each other. The dual leg loop structure 20 shown in FIG. 1 will be called a "full-loop" structure.

The far ends of the spline legs 22 radiate from a distal hub 24. The near ends of the spline legs 22 radiate from a base 26 attached to the distal end 16 of the catheter tube 12. The multiple electrode elements 28 are arranged along each spline leg 22.

Figure 2:
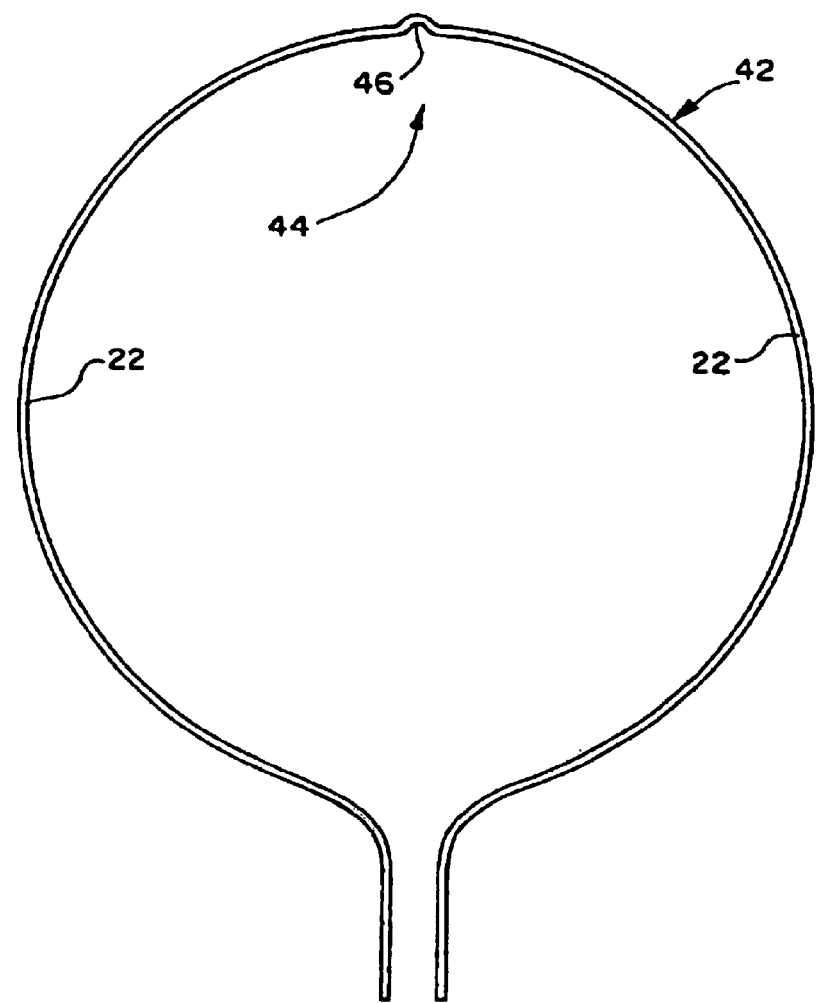
FIG. 2 is an elevation view of a spline used to form the loop structure shown in FIG. 1.

In one implementation, the two spline legs 22 of the structure 20 are paired together in an integral loop body 42 (see FIG. 2). Each body 42 includes a mid-section 44 from which the spline elements 22 extend as an opposed pair of legs. As FIG. 2 shows, the mid-section 44 includes a preformed notch or detent 46, whose function will be described later.

The loop body 42 is preferably made from resilient, inert wire, like Nickel Titanium (commercially available as Nitinol material). However, resilient injection molded inert plastic or stainless steel can also be used. Preferably, the spline legs 22 comprise thin, rectilinear strips of resilient metal or plastic material. Still, other cross sectional configurations can be used.

In this implementation (see FIGS. 3 and 4), the distal hub 24 has a generally cylindrical side wall 50 and a rounded end wall 52. A longitudinal slot 56 extends through the hub 24, diametrically across the center bore 54.

In the illustrated embodiment, the hub 24 is made of an inert, machined metal, like stainless steel. The bore 54 and slot 56 can be formed by conventional EDM techniques. Still, inert molded plastic materials can be used to form the hub 24 and associated openings.

In this implementation, to assemble the structure 20 (see FIGS. 4 and 5), a spline leg 22 of the hoop-like body 42 is inserted through the slot 56 until the mid-body section 44 enters the bore 54. The detent 46 snaps into the bore 54 (see FIG. 4) to lock the body 42 to the hub 24, with the opposed pair of spline legs 22 on the body 42 radiating free of the slot 56 (see FIG. 5).

Figure 5:
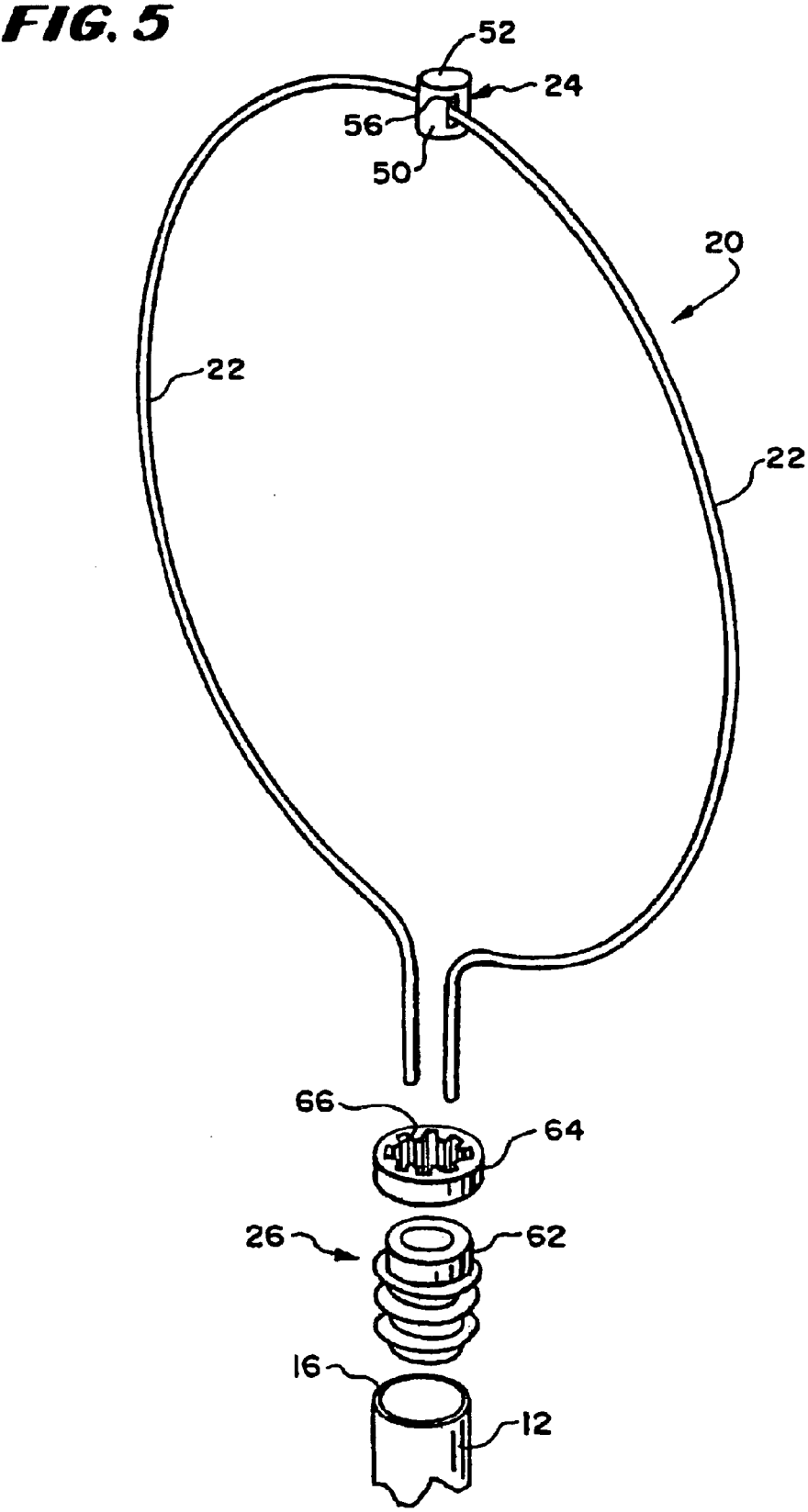
FIG. 5 is a perspective, partially exploded view of the spline, distal hub, and base assembly used to form the loop structure shown in FIG. 1.
Figure 6A:
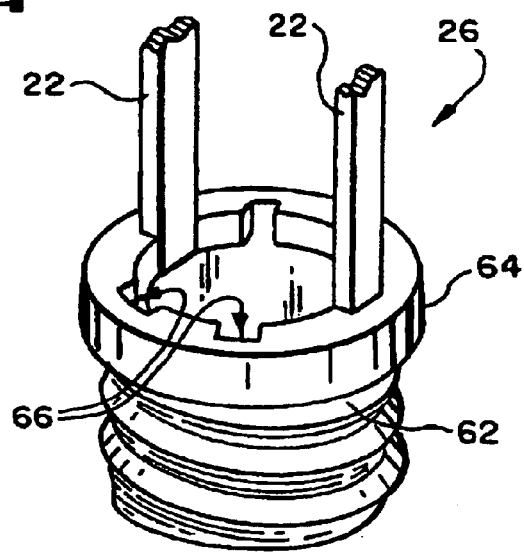
FIG. 6A is an enlarged perspective view of the base assembly shown in FIG. 5.
Figure 6B:
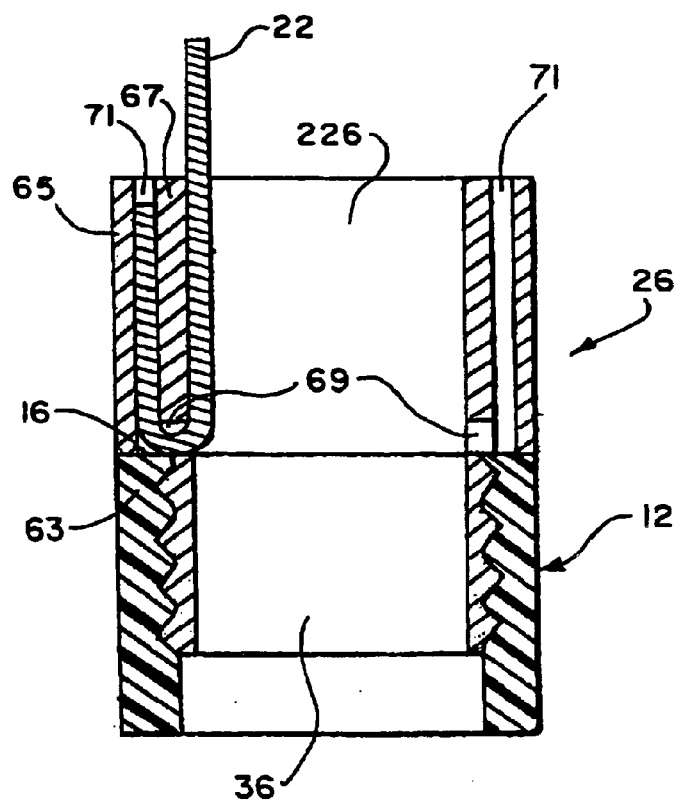
FIG. 6B is a side section view of an alternative base assembly for the loop structure shown in FIG. 1.

In the illustrated embodiment (see FIGS. 5 and 6A), the base 26 includes an anchor member 62 and a mating lock ring 64. The anchor member 62 fits with an interference friction fit into the distal end 16 of the catheter tube 12. The lock ring 64 includes a series of circumferentially spaced grooves 66 into which the free ends of the spline legs 22 fit. The lock ring 64 fits about the anchor member 62 to capture with an interference fit the free ends of the spline legs 22 between the interior surface of the grooves 66 and the outer surface of the anchor member 62 (see FIG. 6). The anchor member 62/lock ring 64 assembly holds the spline elements 22 in a desired flexed condition.

In an alternative construction (see FIG. 6B), the base 26 can comprise a slotted anchor 63 carried by the distal end 16 of the cathetertube 12. The slotted anchor 63 is made of an inert machined metal or molded plastic material. The slotted anchor 63 includes an outer ring 65 and a concentric slotted inner wall 67. The interior of the anchor 63 defines an open lumen 226 to accommodate passage of wires and the like between the catheter tube bore 36 and the support structure 20 (as will be described in greater detail later).

The inner wall 67 includes horizontal and vertical slots 69 and 71 for receiving the free ends of the spline legs 22. The free ends pass through the horizontal slots 69 and are doubled back upon themselves and wedged within the vertical slots 71 between the outer ring 65 and the inner wall 67, thereby securing the spline legs 22 to the anchor 63.

There are other alternative ways of securing the spline legs 22 to the distal end 16 of the catheter tube 12, which will be described later.

Figure 3:
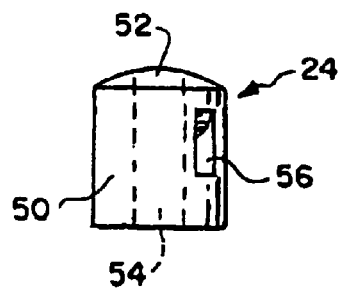
FIG. 3 is an elevation view of the distal hub used to form the loop structure shown in FIG. 1.
Figure 10:
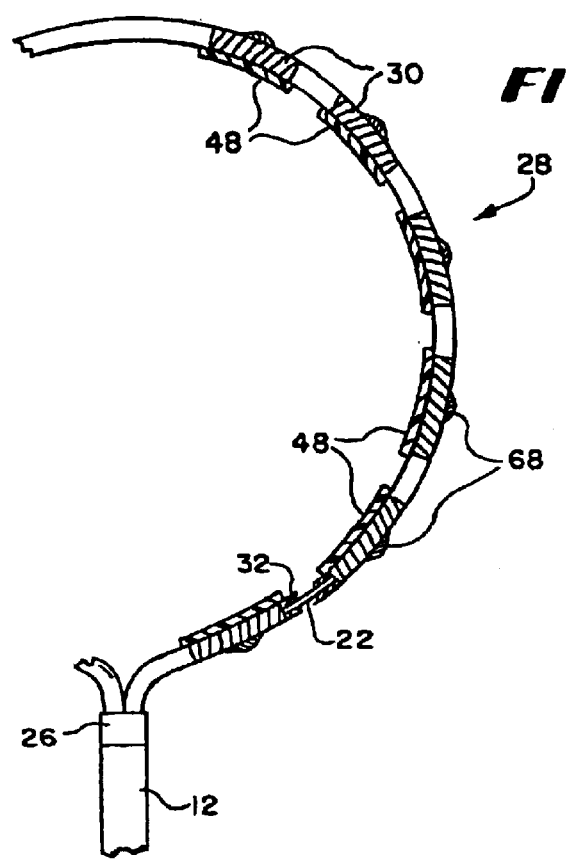
FIG. 10 is an elevation view, with parts broken away, of multiple electrode elements comprising segmented rings carried by a loop support structure.
Figure 11B:
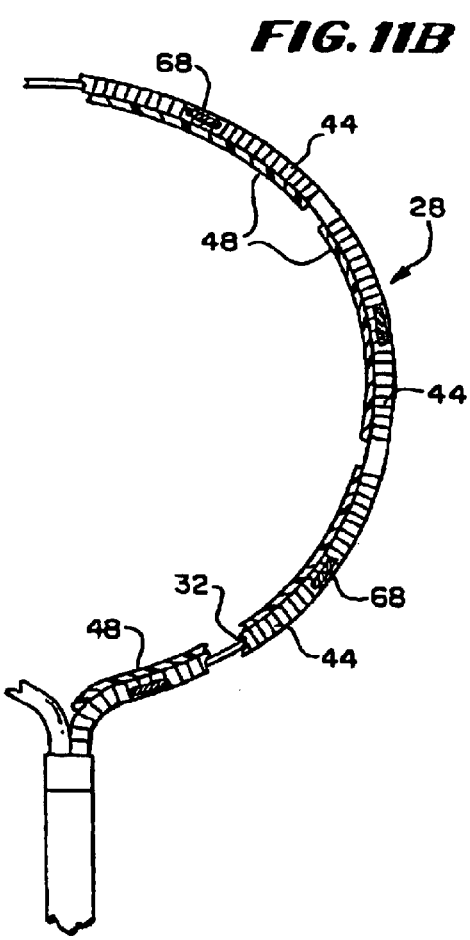
FIG. 11B is an elevation view, with parts broken away, of multiple electrode elements comprising wrapped coils carried by a loop support structure.

Preferably, the full-loop structure 20 shown in FIG. 1 does not include a hub 24 like that shown in FIGS. 1 and 3, and, in addition, does not incorporate a detented integral loop body 42 like that shown in FIG. 2. Any single full-loop structure without a center stiffener or stylet (as will be described later) preferably comprises a single length of resilient inert wire (like Nickel Titanium) bent back upon itself and preformed with resilient memory to form the desired full loop shape. Structure 112 in FIG. 29 (which will be described in greater detail later) exemplifies the use of a preshaped doubled-back wire to form a loop, without the use of a hub 24 or detented loop body 42. FIGS. 10 and 11B also show a portion of the doubled-back wire embodiment, free of the hub 24.

FIG. 7 shows an alternative loop structure 20(1) that includes a single spline leg 22(1) carrying multiple electrode elements 28. This single leg loop structure will be called a "half-loop" structure, in contrast to the dual leg loop structure 20 (i.e., the "full-loop structure) shown in FIG. 1.

In assembling the half-loop structure 20(1) shown in FIG. 7, the hoop-like body 42 shown in FIG. 2 is cut on one side of the detent 46 to form the single spline leg 22(1). The single spline leg 22(1) is snap-fitted into the hub 24 and captured with an interference fit by the anchor member 62/lock ring 64 assembly of the base 26 in the manner just described (shown in FIGS. 5 and 6A). Alternatively, the single spline leg 22(1) can be wedged within the base anchor ring 63 shown in FIG. 6B. In FIG. 7, the half-loop structure 20(1) also includes a center stiffener 40 secured to the base 26 and to the bore 54 of the hub 24. The stiffener 40 can be made of a flexible plastic like Fortron, or from a hollow tube like hypo-tubing or braid plastic tubing.

It should be appreciated that other loop-type configurations besides the full-loop structure 20 and half-loop structure 20(1) are possible. For example, two half-loop structures 20(1), one or both carrying electrode elements 28, can be situated in circumferentially spaced apart positions with a center stiffener 40, as FIG. 8 shows. As another example, four half-loop structures, or two full-loop structures can be assembled to form a three-dimensional, basket-like structure 60 (without using a center stiffener 40), like that shown in FIG. 9.

Regardless of the configuration, the loop structure provides the resilient support necessary to establish and maintain contact between the electrode elements 28 and tissue within the body.

The electrode elements 28 can serve different purposes. For example, the electrode elements 28 can be used to sense electrical events in heart tissue. In the illustrated and preferred embodiments, the principal use of the electrode elements 28 is to emit electrical energy to ablate tissue. In the preferred embodiments, the electrode elements 28 are conditioned to emit electromagnetic radio frequency energy.

The electrode elements 28 can be assembled in various ways.

In one preferred embodiment (see FIG. 10), the elements comprise multiple, generally rigid electrode elements 30 arranged in a spaced apart, segmented relationship upon a flexible, electrically nonconductive sleeve 32 which surrounds the underlying spline leg 22. The sleeve 32 is made a polymeric, electrically nonconductive material, like polyethylene or polyurethane.

The segmented electrodes 30 comprise solid rings of conductive material, like platinum. The electrode rings 30 are pressure fitted about the sleeve 32. The flexible portions of the sleeve 32 between the rings 30 comprise electrically nonconductive regions. Alternatively, the electrode segments 30 can comprise a conductive material, like platinum-iridium or gold, coated upon the sleeve 32 using conventional coating techniques or an ion beam assisted deposition (IBAD) process. For better adherence, an undercoating of nickel ortitanium can be applied. The electrode coating can be applied either as discrete, closely spaced segments or in a single elongated section.

In a more preferred embodiment (see FIGS. 11A and 11B), spaced apart lengths of closely wound, spiral coils are wrapped about the sleeve 32 to form an array of segmented, generally flexible electrodes 34. The coil electrodes 34 are made of electrically conducting material, like copper alloy, platinum, or stainless steel. The electrically conducting material of the coil electrode 34 can be further coated with platinum-iridium or gold to improve its conduction properties and biocompatibility.

The inherent flexible nature of a coiled electrode structures 34 also makes possible the construction of a continuous flexible ablating element comprising an elongated, closely wound, spiral coil of electrically conducting material, like copper alloy, platinum, or stainless steel, wrapped about all or a substantial length of the flexible sleeve 32.

The electrode elements 28 can be present on all spline legs 22, as FIG. 1 shows, or merely on a selected number of the spline legs 22, with the remaining spline legs serving to add structural strength and integrity to the structure.

Figure 11A:
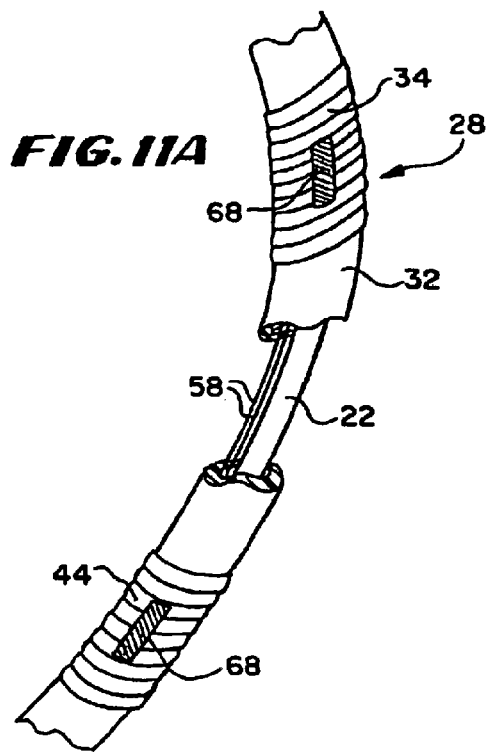
FIG. 11A is an enlarged view, with parts broken away, of multiple electrode elements comprising wrapped coils carried by a loop support structure.

The electrode elements 28 are electrically coupled to individual wires 58 (see FIG. 11A) to conduct ablating energy to them. The wires 58 extend along the associated spline leg 22 (as FIG. 11A shows), through a suitable access opening provided in the base 24 (for example, the anchor lumen 226 shown in FIG. 6B) into and through the catheter body lumen 36 (as generally shown in FIG. 1 and FIGS. 30A/B), and into the handle 18, where they are electrically coupled to external connectors 38 (see FIG. 1). The connectors 38 plug into a source of RF ablation energy (not shown).

Various access techniques can be used to introduce the probe 10 and its loop support structure 20 into the desired region of the heart. For example, to enter the right atrium, the physician can direct the probe 10 through a conventional vascular introducer through the femoral vein. For entry into the left atrium, the physician can direct the probe 10 through a conventional vascular introducer retrograde through the aortic and mitral valves.

Alternatively, the physician can use the delivery system shown in pending U.S. application Ser. No. 08/033,641, filed Mar. 16, 1993, and entitled "Systems and Methods Using Guide Sheaths for Introducing, Deploying, and Stabilizing Cardiac Mapping and Ablation Probes."

In use, the physician verifies contact between the electrode elements 28 and heart tissue using conventional pacing and sensing techniques. Once the physician establishes contact with tissue in the desired heart region, the physician applies ablating energy to the electrode elements 28.

The electrode elements 28 can be operated in a uni-polar mode, in which the ablation energy emitted by the electrode elements 28 is returned through an indifferent patch electrode attached to the skin of the patient (not shown). Alternatively, the elements 28 can be operated in a bi-polar mode, in which ablation energy emitted by one element 28 is returned through another element 28 on the spline leg 22.

The size and spacing of the electrode elements 28 shown in FIGS. 10 and 11A/B are well suited for creating continuous, long and thin lesion patterns in tissue when ablation energy is applied simultaneously to adjacent emitting electrode elements 28. Continuous lesion patterns uniformly result when adjacent electrode elements 28 (i.e., the segments 30 or coils 34) are spaced no farther than about 2.5 times the electrode segment diameter apart. Further details of the formation of continuous, long and thin lesion patterns are found in copending U.S. patent application Ser. No. 08/287,192, filed Aug. 8, 1994, entitled "Systems and Methods for Forming Elongated Lesion Patterns in Body Tissue Using Straight or Curvilinear Electrode Elements," which is incorporated herein by reference.

Using rigid electrode segments 30, the length of the each electrode segment can vary from about 2 mm to about 10 mm. Using multiple rigid electrode segments longer than about 10 mm each adversely effects the overall flexibility of the element. Generally speaking, adjacent electrode segments 30 having lengths of less than about 2 mm do not consistently form the desired continuous lesion patterns.

When flexible electrode segments 34 are used, electrode segments longer that about 10 mm in length can be used. Flexible electrode segments 34 can be as long as 50 mm. If desired, the flexible electrode structure 34 can extend uninterrupted along the entire length of the support spline 22.

The diameter of the electrode segments 30 or 34 and underlying spline leg 22 (including the flexible sleeve 32) can vary from about 2 French to about 10 French.

Preferably (as FIGS. 10 and 11B show), the side of the ablation elements 28 that, in use, is exposed to the blood pool is preferably covered with a coating 48 of an electrically and thermally insulating material. This coating 48 can be applied, for example, by brushing on a UV-type adhesive or by dipping in polytetrafluoroethylene (PTFE) material.

The coating 48 prevents the transmission of ablating energy directly into the blood pool. Instead, the coating 48 directs the applied ablating energy directly toward and into the tissue.

The focused application of ablating energy that the coating 48 provides helps to control the characteristics of the lesion. The coating 48 also minimizes the convective cooling effects of the blood pool upon the ablation element while ablating energy is being applied, thereby further enhancing the efficiency of the lesion formation process.

In the illustrated and preferred embodiments (see FIGS. 10 and 11A/B), each flexible ablation element carries at least one and, preferably, at least two, temperature sensing elements 68. The multiple temperature sensing elements 68 measure temperatures along the length of the electrode element 28. The temperature sensing elements 68 can comprise thermistors or thermocouples.

An external temperature processing element (not shown) receives and analyses the signals from the multiple temperature sensing elements 68 in prescribed ways to govern the application of ablating energy to the flexible ablation element. The ablating energy is applied to maintain generally uniform temperature conditions along the length of the element.

Further details of the use of multiple temperature sensing elements in tissue ablation can be found in copending U.S. patent application Ser. No. 08/286,930, filed Aug. 8, 1994, entitled "Systems and Methods for Controlling Tissue Ablation Using Multiple Temperature Sensing Elements."

To aid in locating the structure 20 within the body, the handle 16 and catheter body 12 preferably carry a steering mechanism 70 (see FIGS. 1 and 12) for selectively bending or flexing the distal end 16 of the catheter body 12.

The steering mechanism 18 can vary. In the illustrated embodiment (see FIG. 12), the steering mechanism 70 includes a rotating cam wheel 72 with an external steering lever 74 (see FIG. 1). As FIG. 12 shows, the cam wheel 72 holds the proximal ends of right and left steering wires 76. The steering wires 76, like the signal wires 58, pass through the catheter body lumen 36. The steering wires 76 connect to the left and right sides of a resilient bendable wire or spring (not shown) enclosed within the distal end 16 of the catheter body 12. Forward movement of the steering lever 74 flexes or curves the distal end 16 down. Rearward movement of the steering lever 74 flexes or curves the distal end 16 up.

Further details of this and other types of steering mechanisms are shown in Lundquist and Thompson U.S. Pat. No. 5,254,088, which is incorporated into this Specification by reference.

II. Variable Shape Loop Support Structures

To uniformly create long, thin lesions having the desired therapeutic effect, the loop support structure 20 or 20(1) must make and maintain intimate contact between the electrode elements 28 and the endocardium.

The invention provides loop support structures that the physician can adjust to adapt to differing physiologic environments.

A. Distended Loop Structures

The adjustable loop structure 78 shown in FIG. 13 is in many respects similar to the full-loop structure 20 shown in FIG. 1. The adjustable full-loop structure 78 includes the pair of diametrically opposite spline legs 22 that radiate from the base 26 and hub 24.

In addition, the adjustable full-loop structure 78 includes a flexible stylet 80 attached at its distal end to the hub bore 54. The stylet 80 can be made from a flexible plastic material, like Fortron, or from a hollow tube, like hypotubing or braid plastic tubing.

The stylet 80 extends along the axis of the structure 78, through the base 26 and catheter body lumen 36, and into the handle 18. In this arrangement, the stylet 80 is free to slide fore and aft along the axis of the catheter body 12.

The proximal end of the stylet 80 attaches to a control knob 82 in the handle 18 (as FIG. 13 shows). The control knob 82 moves within a groove 84 (see FIGS. 13 and 14) in the handle 18 to impart fore and aft movement to the stylet 80. Stylet movement changes the flexure of the structure 78.

Forward movement of the stylet 80 (i.e., toward the distal end 16) pushes the hub 24 away from the base 26 (see FIG. 15). The loop structure 78 elongates as the spline legs 22 straighten and move radially inward, to the extent permitted by the resilience of the spline legs 22. With the spline legs 22 straightened, the loop structure 78 presents a relatively compact profile to facilitate vascular introduction.

Rearward movement of the stylet 80 (i.e., toward the distal end 16) pulls the hub 24 toward the base 26 (see FIG. 16). The spline legs 22 bend inward in the vicinity of the hub 24, while the remainder of the splines, constrained by the base, distend. The loop structure 78 bows radially out to assume what can be called a "heart" shape.

When the structure 78 is positioned within the atrium 88 of a heart in the condition shown in FIG. 16, the stylet 80 compresses the spline legs 22, making them expand or bow radially. The expansion presses the distended midportion of the spline legs 22 (and the electrode elements 28 they carry) symmetrically against opposite walls 86 of the atrium 88. The symmetric expansion of the outwardly bowed spline legs 22 presses the opposite atrial walls 86 apart (as FIG. 16 shows), as the radial dimension of the loop structure 78 expands to span the atrium 88.

The symmetric expansion presses the electrode elements 28 into intimate surface contact against the endocardium. The symmetric expansion stabilizes the position of the loop structure 78 within the atrium 88. The resilience of the spline legs 22, further compressed by the pulled-back stylet 80, maintains intimate contact between the electrode elements 28 and atrial tissue, without trauma, as the heart expands and contracts.

As FIGS. 17 to 19 show, the push-pull stylet 80 can also be used in association with a half-loop structure 90, like that previously shown and discussed in FIG. 7. In this arrangement, the movable stylet 80 substitutes for the flexible, but otherwise fixed stiffener 40.

In this arrangement, pushing the stylet 80 forward (as FIG. 18 shows) elongates the half-loop structure 90 for vascular introduction. Pulling the stylet 80 rearward (as FIG. 19 shows) bows the single spline leg 22 of the structure outward, expanding it so that more secure contact can be achieved against the atrial wall 86, or wherever tissue contact is desired.

B. Curvilinear Loop Structures

Figure 21:
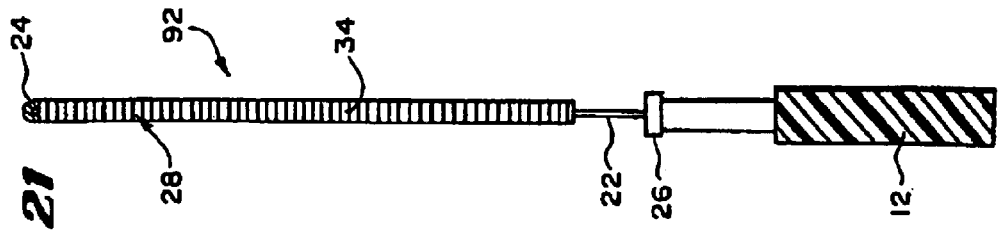
FIG. 21 is a side elevation view of the full-loop structure shown in FIG. 20.
Figure 20:
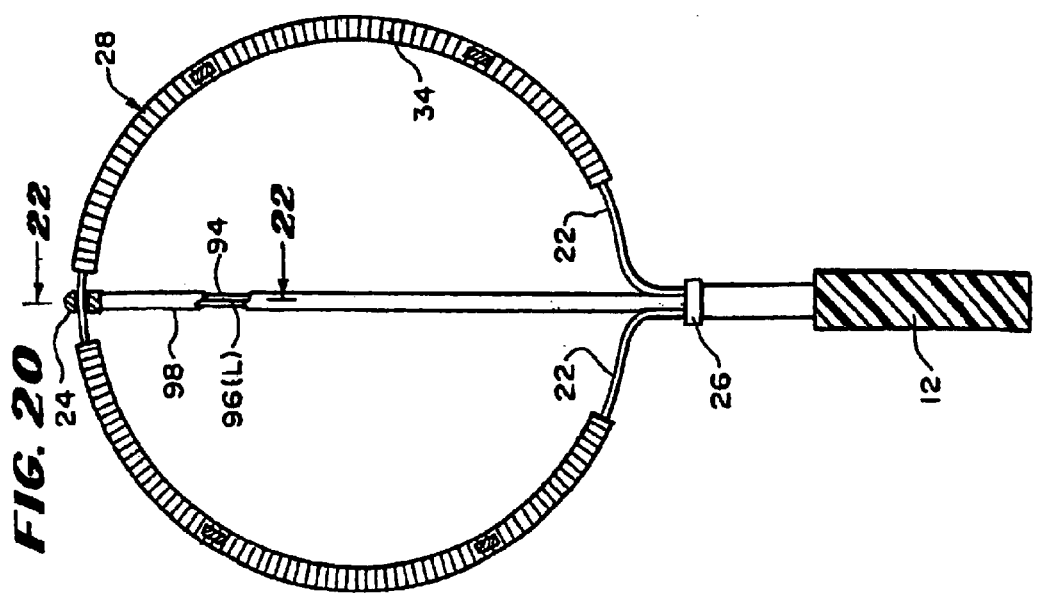
FIG. 20 is a plan view of a full-loop structure for supporting multiple electrode elements having an associated center stylet attached to a remote control knob for movement to extend and distend the full-loop structure, and also having a remotely controlled steering mechanism to flex the center stylet to bend the full-loop structure into a curvilinear shape.

FIGS. 20 and 21 show a full-loop structure 92 that includes a center stylet 94, which can be flexed. The flexing of the center stylet 94 bends the spline legs 22 in a second direction different than the radial direction in which they are normally flexed. In the illustrated embodiment, this second direction is generally perpendicular to the axes of the spline legs 22, as FIGS. 23A/B and 24 show, although acute bends that are not generally perpendicular can also be made. The bending of the spline legs 22 in this fashion makes possible the formation of long, thin curvilinear lesions using a full-loop structure 92, or (as will be described later) in a half-loop structure 110, as well.

The stylet 94 itself can be either fixed in position between the hub 24 and the base 26, or movable along the axis of the loop structure 92 to extend and distend the radial dimensions of the spline legs 22 in the manner already described (see FIGS. 15 and 16). In the illustrated and preferred embodiment, the stylet 94 slides to alter the radial dimensions of the structure.

Figure 22:
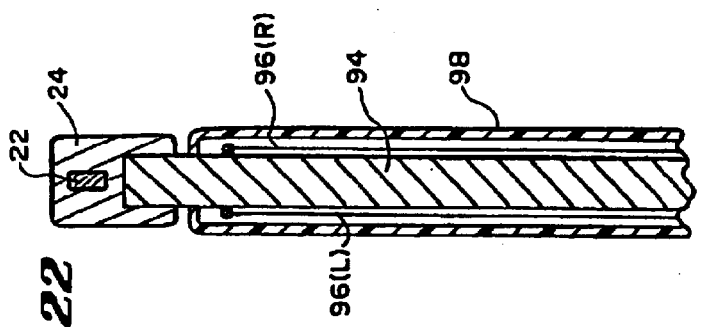
FIG. 22 is an enlarged sectional view, generally taken along line 22—22 in FIG. 20, showing the steering wires attached to the center stylet to flex it.

In one implementation, as FIG. 22 best shows, the stylet 94 is made from a metal material, for example stainless steel 17-7, Elgiloy™ material, or Nickel Titanium material. A pair of left and right steering wires, respectively 96(R) and 96(L) is attached to opposite side surfaces of the stylet 94 near the hub 24, by adhesive, soldering, or by suitable mechanical means. The steering wires 96(R) and 96(L) are attached to the stylet side surfaces in a diametric opposite orientation that is at right angles to the radial orientation of the spline legs 22 relative to the stylet 94.

The steering wires 96(R) and 96(L) extend along the stylet 94, through the base 26 and catheter body lumen 36, and into the handle 18 (see FIG. 25). Preferable, as FIG. 22 best shows, a tube 98 surrounds the stylet 94 and steering wires 96(R) and 96(L), at least along the distal, exposed part of the stylet 94 within the structure 92, keeping them in a close relationship. The tube 98 can be heat shrunk to fit closely about the stylet 94 and steering wires 96(R) and 96(L).

As FIGS. 25 and 26 show, a groove 100 in the handle carries a control assembly 102. The stylet 94 is attached to the control assembly 102, in the manner already described with respect to the control knob 82 in FIGS. 13 and 14. Sliding movement of the control assembly 102 within the groove 100 imparts fore and aft movement to the stylet 94, thereby distending or extending the loop structure 92.

The control assembly 102 further includes a cam wheel 104 (see FIG. 26) rotatable about an axle on the control assembly 102 in response to force applied to an external steering lever 108. The cam wheel 104 holds the proximal ends of the steering wires 96(R) and 96(L), in the manner disclosed in Lundquist and Thompson U.S. Pat. No. 5,254,088, already discussed, which is incorporated herein by reference.

Twisting the steering lever 108 counterclockwise applies tension to the left steering wire 96(L), bending the loop structure 92 to the left (as FIG. 23A shows). The electrode elements 28 (which in FIGS. 20 to 27 comprises a continuous coil electrode 34, described earlier) likewise bend to the left.

Similarly, twisting the steering lever 108 clockwise applies tension to the right steering wire 96(R), bending the loop structure 92 to the right (as FIGS. 23B and 24 show). The electrode elements 28 likewise bend to the right.

The bent electrode elements 28, conforming to the bent spline legs 22, assume different curvilinear shapes, depending upon amount of tension applied by the steering wires 96(R) and 96(L). When contacting tissue, the bent electrode elements 28 form long, thin lesions in curvilinear patterns.

In an alternative implementation, the stylet 94 is not flexible and remotely steerable, but is instead made of a malleable metal material, like annealed stainless steel. In this arrangement, before deployment in the body, the physician applies external pressure to manually bend the stylet 94 into a desired shape, thereby imparting a desired curvilinear shape to the electrode elements of the associated loop structure. The malleable material of the stylet 94 retains the preformed shape, until the associated loop structure is withdrawn from the body and sufficient external pressure is again applied by the physician to alter the stylet shape.

In addition to having a malleable stylet 94, the splines 22 themselves can also be made of a malleable material, like annealed stainless steel, or untreated stainless steel 17-7, or untreated Nickel Titanium. In one implementation, the most distal parts of the malleable splines 22 are heat treated to maintain their shape and not collapse during introduction and deployment in the vascular system. This will also give the overall structure greater stiffness for better contact with the tissue. It also gives the physician the opportunity to bend the structure to form long, thin, lesions in prescribed curvilinear patterns set by the malleable splines.

Whether flexible and remotely flexed during deployment, or malleable and manually flexed before deployment, by further adjusting the fore-and-aft position of the stylet 94, the physician can also control the radial dimensions of the loop structure 94 in concert with controlling the curvilinear shape of the loop structure 92, as FIG. 27 shows. A diverse array of radial sizes and curvilinear shapes is thereby available.

As FIG. 28 shows, a half-loop structure 110 can also include a fixed or movable stylet 94 with steering wires 96(R) and 96(L). The use of the same handle-mounted control assembly 102/rotatable cam 104 assembly shown in FIGS. 25 and 26 in association with the half-loop structure 110 makes possible the creation of diverse curvilinear shapes of variable radii. Alternatively, a malleable stylet 94 and malleable splines can be used.

C. Loop Structures with Movable Spline Legs

FIGS. 29 to 35 show a full-loop structure 112 in which only one spline leg 114 is attached to the base 26. The fixed spline leg 114 is preformed with resilient memory to assume a curve of a selected maximum radius (shown in FIG. 33). The other spline leg 116, located diametrically opposed to the fixed spline leg 114, extends through the base 26 and catheter body lumen 36 (see FIGS. 30A and 30B) into the handle 18. The spline leg 116 slides fore and aft with respect to the base 26. Movement of the spline leg 116 changes the flexure of the structure 112.

The full-loop structure 112 shown in FIGS. 29 to 35 need not include a hub 24 like that shown in FIGS. 1 and 3, and, in addition, need not incorporate a detented integral loop body 42 like that shown in FIG. 2. Any single full-loop structure without a center stiffener or stylet, like the structure 112 in FIG. 29, can comprise a single length of wire bent back upon itself and preformed with resilient memory to form the desired full loop shape. For the same reason, the single full-loop structure 20 shown in FIG. 1 can, in an alternative construction, be made without a hub 24 and a detented loop body 42, and instead employ a preshaped doubled-back wire to form a loop, like the structure 20.

FIG. 30B shows an alternative way of securing the fixed spline leg 114 to the distal end 16 of the catheter tube 12, without using a base 26. In this embodiment, the free end of the fixed spline leg 114 lies against the interior of the tube 12. The leg 114 passes through a slit 115 formed in the catheter tube 12. The leg 114 is bent back upon itself in a u-shape to lie against the exterior of the tube 12, wedging the tube 12 within the u-shape bend 117. A sleeve 119 is heat shrunk about the exterior of the tube 12 over the region where the u-shape bend 117 of the spline leg 114 lies, securing it to the tube 12. Alternatively, a metallic ring (not shown) can be used to secure the spline leg 114 to the tube 12. The movable spline leg 116 and wires 58 pass through the interior bore 36 of the catheter tube 12, as before described.

The proximal end of the spline leg 116 (see FIG. 29) is attached to a movable control knob 82 carried in a groove 84 on the handle 18, like that shown in FIG. 13. Movement of the control knob 82 within the groove 84 thereby imparts fore-and-aft movement to the spline leg 116.

In the illustrated embodiment, the fixed spline leg 114 carries electrode elements 28 in the manner already described. The movable spline leg 116 is free of electrode elements 28. Still, it should be appreciated that the movable spline leg 116 could carry one or more electrode elements 28, too.

As FIGS. 31 to 33 show, moving the control knob 82 forward slides the movable spline leg 116 outward, and vice versa. The movable spline leg 116 applies a counter force against the resilient memory of the fixed spline leg 114, changing the flexure and shape of the loop structure 112 for vascular introduction and deployment in contact with tissue. By pulling the movable spline leg 116 inward (as FIG. 31 shows), the counter force contracts the radius of curvature of the fixed spline leg 114 against its resilient memory. Pushing the movable spline leg 116 outward (as FIGS. 32 and 33 show) allows the resilient memory of the fixed spline leg 114 to expand the radius of curvature until the selected maximum radius is achieved. The counter force applied changes the flexure and shapes the fixed spline leg 114 and the electrode elements 28 it carries to establish and maintain more secure, intimate contact against atrial tissue.

The magnitude (designated V in FIGS. 31 to 33) of the counter force, and the resulting flexure and shape of the loop structure 112, varies according to extent of outward extension of the movable spline leg 116. Pulling the movable spline leg 116 progressively inward (thereby shortening its exposed length) (as FIG. 31 shows) contracts the loop structure 112, lessening its diameter and directing the counter force progressively toward the distal end of the structure. Pushing the movable spline leg 116 progressively outward (thereby lengthening its exposed length) (as FIGS. 32 and 33 show) progressively expands the loop structure 112 in response to the resilient memory of the fixed spline leg 114, increasing its diameter and directing the counter force progressively away from the distal end of the structure.

As FIGS. 34 and 35 show, by manipulating the movable spline leg 116, the physician can adjust the flexure and shape of the loop structure 112 within the atrium 88 from one that fails to make sufficient surface contact between the electrode element 28 and the atrial wall 86 (as FIG. 34 shows) to one that creates an extended region of surface contact with the atrial wall 86 (as FIG. 35 shows).

Figure 36:
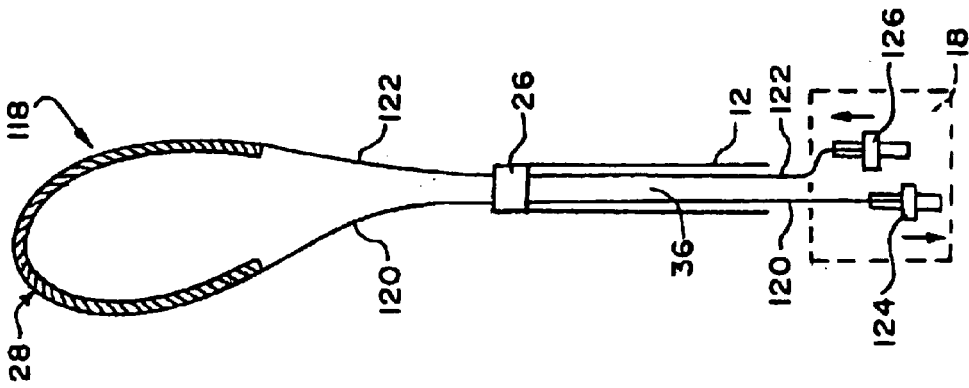
FIGS. 36, 37, and 38 are plan, partially diagrammatic views of a full-loop structure for supporting multiple electrode elements having two movable spline legs attached to remote control knobs for coordinated movement to extend and distend the full-loop structure.
Figure 37:
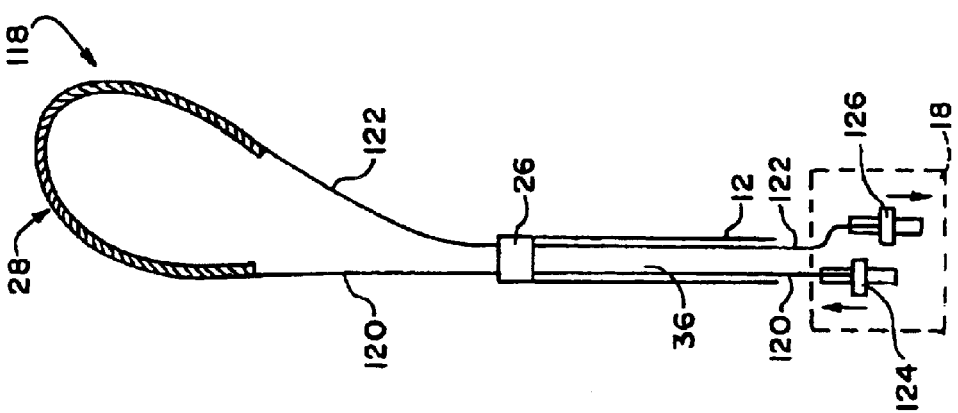
Figure 38:
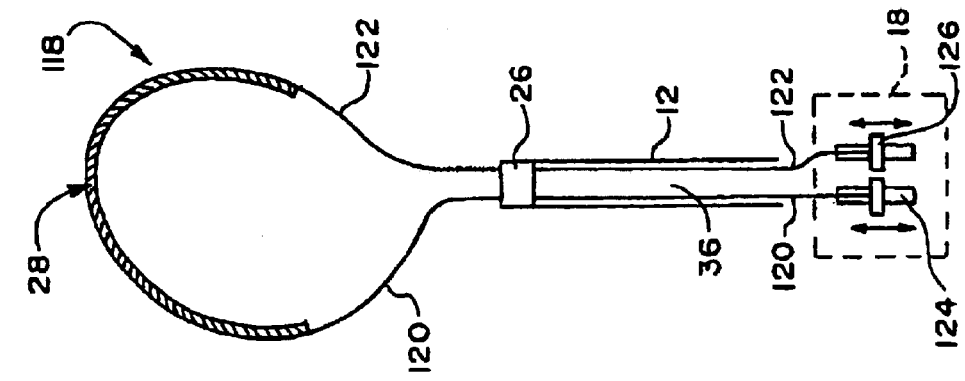

FIGS. 36 to 38 show a full-loop structure 118 in which each spline leg 120 and 122 is independently movable fore and aft with respect to the base 26. In the illustrated embodiment, both spline legs 120 and 122 carry electrode elements 28 in the manner already described.

In this arrangement, the handle 18 includes two independently operable, sliding control knobs 124 and 126 (shown diagrammatically in FIGS. 36 to 38), each one attached to a movable spline leg 120/122, to impart independent movement to the spline legs 120/122 (as shown by arrows in FIGS. 36 to 38). Each spline leg 120/122 is preformed with resilient memory to achieve a desired radius of curvature, thereby imparting a resilient curvature or shape to the full-loop structure 118 itself. Coordinated opposed movement of both spline legs 120/122 (as FIGS. 37 and 38 show) using the control knobs 124/126 allows the physician to elongate the curvature of the loop structure 118 into more of an oval shape, compared to more circular loop structures 112 formed using a single movable leg 116, as FIGS. 31 to 33 show.

Figure 39B:
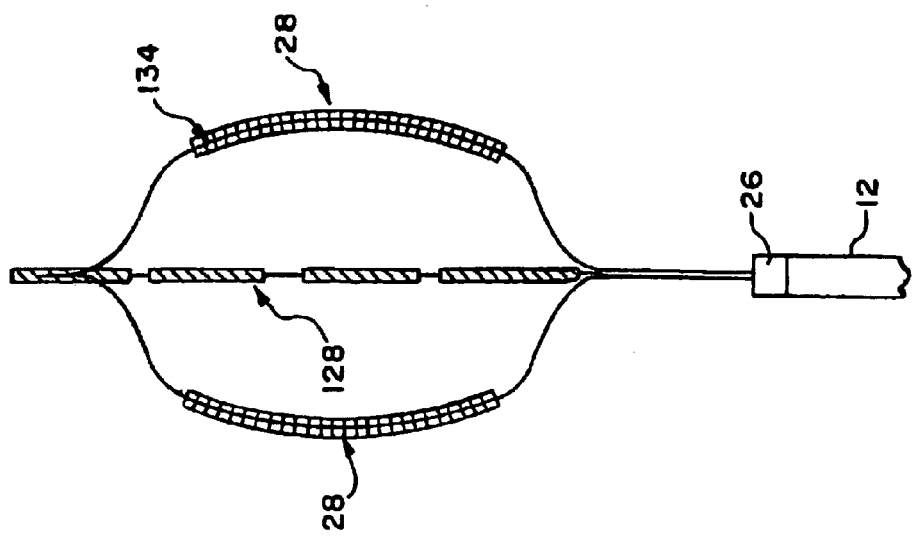
FIG. 39B is a side view of the full-loop structure shown in FIG. 39A, showing the smaller, secondary loop structure.
Figure 39A:
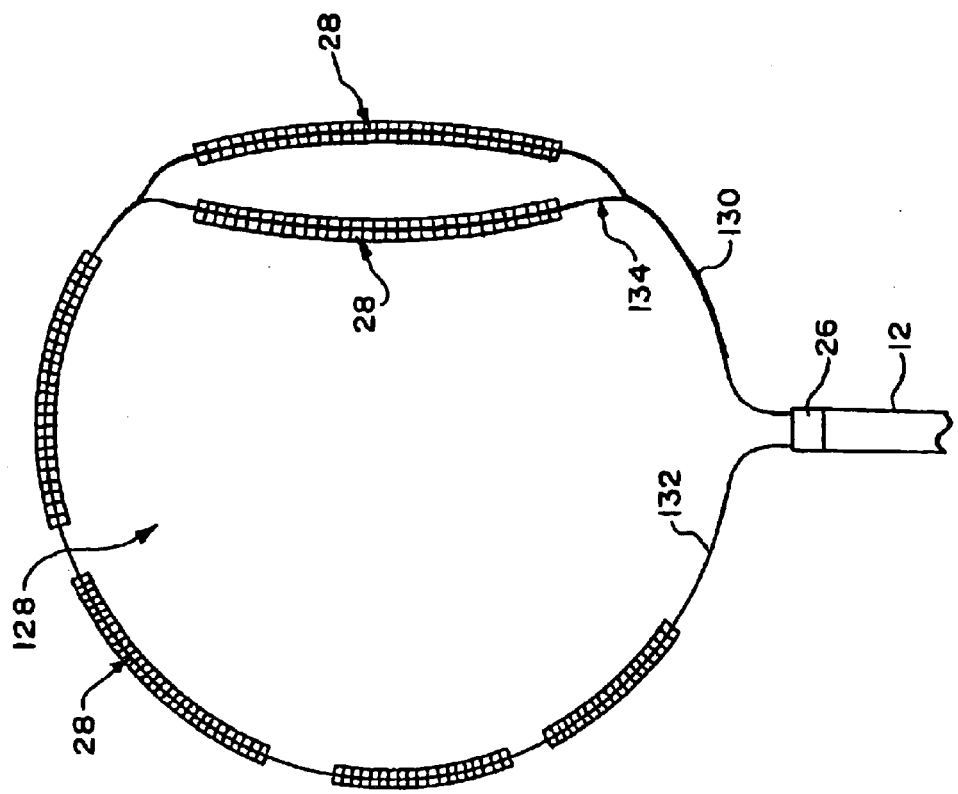
FIG. 39A is a plan view of a full-loop structure for support multiple electrode elements having a smaller, secondary loop structure formed in one spline leg.

FIGS. 39A and 39B show an alternative full-loop structure 128 having one spline leg 130 that is fixed to the base 26 and another spline leg 132, located diametrically opposed to the fixed spline 130, that is movable fore and aft with respect to the base 26 in the manner already described. The movable spline leg 132 can carry electrode elements 28 (as FIG. 39A shows), or be free of electrode elements, depending upon the preference of the physician.

In the structure shown in FIGS. 39A and 39B, the fixed spline leg 130 branches in its midportion to form a smaller, secondary full-loop structure 134 that carries electrode elements 28. In the embodiment shown in FIGS. 39A and 39B, the secondary loop structure 134 lies in a plane that is generally perpendicular to the plane of the main full-loop structure 128.

The smaller, secondary full-loop structure 134 makes possible the formation of annular or circumferential lesion patterns encircling, for example, accessory pathways, atrial appendages, and the pulmonary vein within the heart. In the illustrated embodiment, the movable spline leg 132 compresses the secondary full-loop structure 134, urging and maintaining it in intimate contact with the targeted tissue area.

FIGS. 39A and 39B therefore show a compound flexible support for electrode elements. While the primary support structure 128 and the secondary support structure 134 are shown as full loops, it should be appreciated that other arcuate or non-arcuate shapes can be incorporated into a compound structure. The compound primary structure 128 integrated with a secondary structure 134 need not include a movable spline leg, or, if desired, both spline legs can be movable. Furthermore, a center stylet to contract and distend the main structure 128 can also be incorporated, with or without a stylet steering mechanism.

Figure 40A:
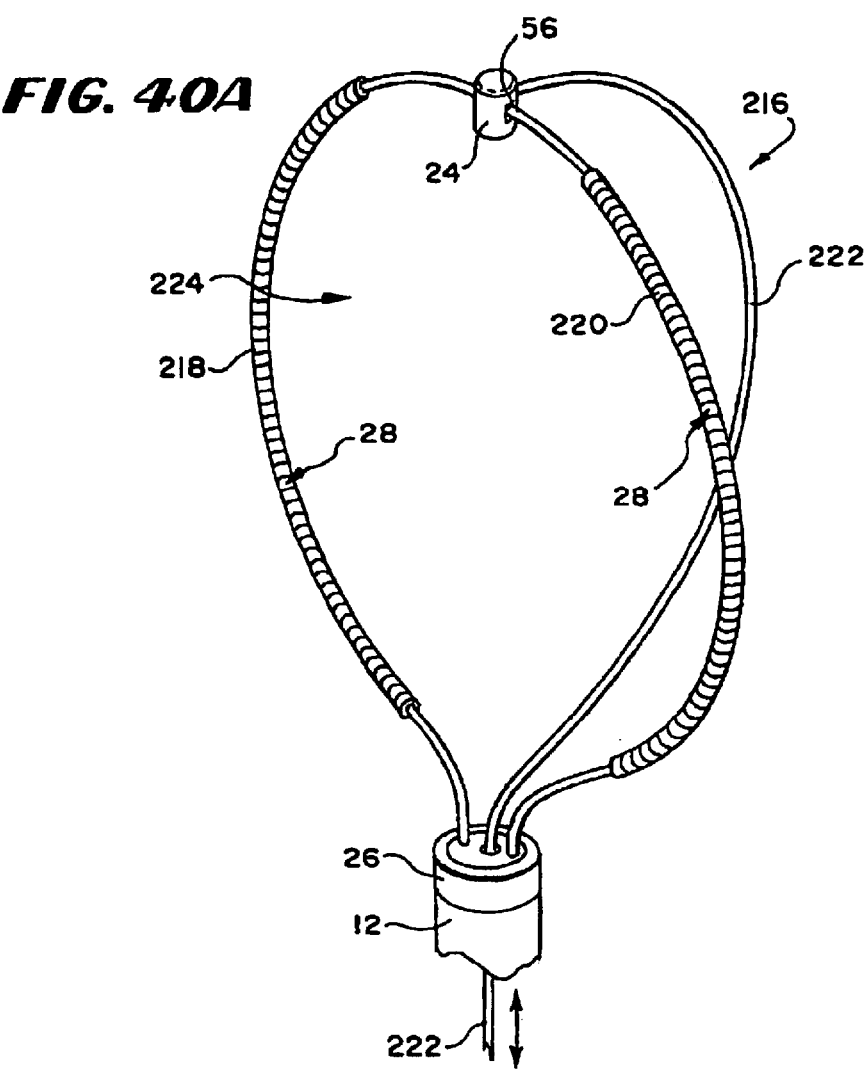
FIG. 40A is a perspective view of a modified full-loop structure for supporting multiple electrode elements having an odd number of three or more spline legs.
Figure 40B:
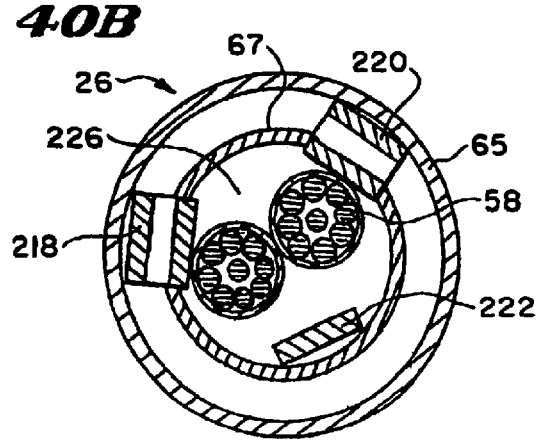
FIG. 40B is a top section view of the base of the full-loop structure shown in FIG. 40A.

FIGS. 40A and B show a modified full-loop structure 216 having an odd number of spline legs 218, 220, and 222. The structure 216 includes two spline legs 218 and 220 that, in the illustrated embodiment, are fixed to the base 26 about 120° apart from each other. As FIG. 40B shows, the base 26 is generally like that shown in FIG. 6B, with the slotted anchor 63 in which the near ends of the legs 218 and 220 are doubled back and wedged. The structure 216 also includes a third spline leg 222 that, in the illustrated embodiment, is spaced about 120° from the fixed spline legs 218/220. As FIG. 40B shows, the near end of the third spline leg 222 is not attached to the base 26, but passes through the inner lumen 226 into the lumen 36 of the catheter tube 12. The third spline leg 222 is thereby movable fore and aft with respect to the base 26 in the manner already described. Alternatively, all spline legs 218, 220, and 222 can be fixed to the base 26, or more than one spline leg can be made moveable.

Figure 4:
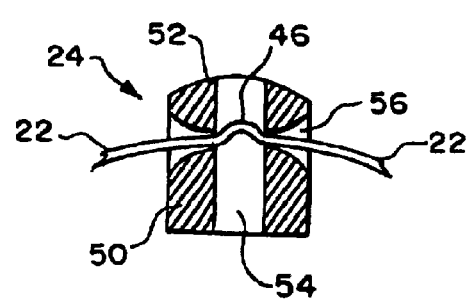
FIG. 4 is a side section view of the hub shown in FIG. 3.

A hub 24 like that shown in FIGS. 3 and 4 includes circumferentially spaced slots 56 to accommodate the attachment of the three splines 218, 220, and 222.

The fixed splines 218 and 220 carry electrode elements 28 (as FIG. 40A shows), while the movable spline 22 is free of electrode elements. As FIG. 40B show, the wires 58 coupled to the electrode elements 28 pass through the anchor lumen 226 for transit through the catheter tube bore 36. The orientation of the fixed splines 218 and 220 relative to the movable spline 222 thereby presents an ablation loop 224, like the secondary loop structure 134 shown in FIGS. 39A/B, that lies in a plane that is generally transverse of the plane of the movable spline 222. Of course, other orientations of an odd number of three or more spline legs can be used.

The movable spline leg 222 extends and compresses the secondary structure 134 to urge and maintain it in intimate contact with the targeted tissue area. Of course, a center stylet to further contract and distend the ablation loop 224 can also be incorporated, with or without a stylet steering mechanism.

D. Bifurcated Loop Structures

Figure 43:
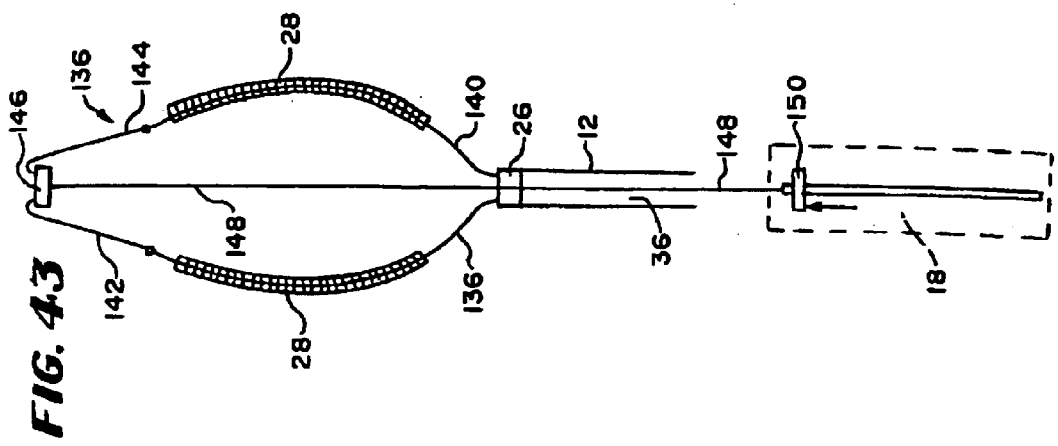
FIGS. 41, 42, and 43 are plan, partially diagrammatic, views of a bifurcated full-loop structure for supporting multiple electrode elements having movable half-loop structures to extend and distend the bifurcated full-loop structure.
Figure 42:
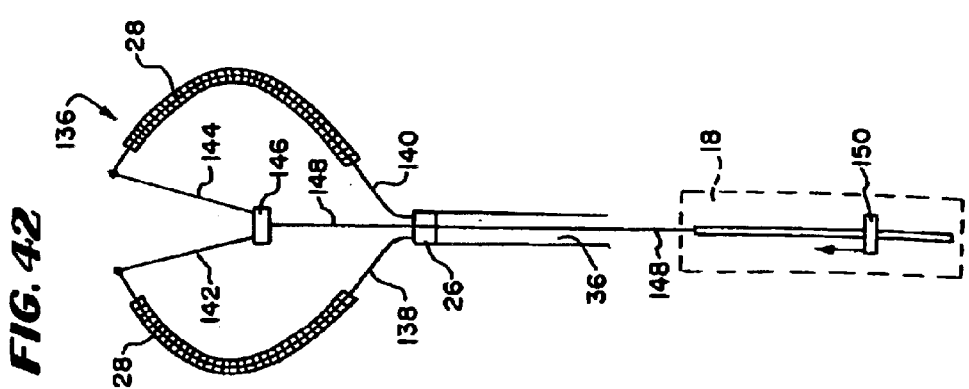
Figure 41:
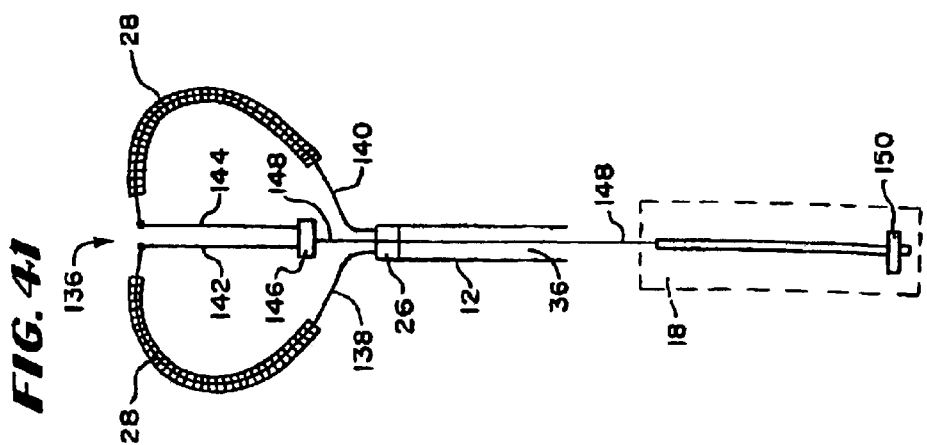

FIGS. 41, 42, and 43 show a variation of a loop structure, which will be called a bifurcated full-loop structure 136. The structure 136 (see FIG. 41) includes two oppositely spaced splines legs 138 and 140, each carrying one or more electrode elements 28. The near end of each spline leg 138/140 is attached to the base 26. The far end of each spline leg 138/140 is attached a stylet 142 and 144. Each spline leg 138/140 is preformed with resilient memory to achieve a desired maximum radius of curvature (which FIG. 41 shows).

The spline leg stylets 142/144 are joined through a junction 146 to a common control stylet 148. The common control stylet 148 passes through the catheter body lumen 36 to a suitable slidable control knob 150 in the handle 18, as already described. By sliding, the control knob 150 moves the control stylet 148 to change the flexure of the spline legs 138/140.

When the control stylet 148 is fully withdrawn, as FIG. 41 shows, the junction 146 is located near the base 26 of the structure 136, and the spline legs 138/140 assume their preformed maximum radii of curvatures. The spline legs 138/140 form individual half-loop structures (like shown in FIG. 7) that together emulate a full-loop structure (like that shown in FIG. 1), except for the presence of a connecting, distal hub 24.

Forward movement of the control stylet 148 first moves the junction 146 within the confines of the structure 136, as FIG. 42 shows. The forward movement of the control stylet 148 is translated by the spline leg stylets 142/144 to urge the spline legs 138/140 apart. The distal end of the bifurcated structure 136 opens like a clam shell.

As the spline legs 138/140 separate, they distend. The control stylet 150 thus compresses the splines legs 138/140 to press them into contact with the tissue area along opposite sides of the structure 136. In this way, the bifurcated structure 136 emulates the full-loop structure 78, when distended (as FIG. 16 shows).

Continued forward movement of the control stylet 150 (as FIG. 43 shows) moves the junction 146 and attached spline leg stylets 142/146 out beyond the confines of the structure 136. This continued forward movement extends the spline legs 136/140, while moving them radially inward. This, in effect, collapses the bifurcated structure 136 into a relatively low profile configuration for vascular introduction. In this way, the bifurcated structure 136 emulates the full-loop structure 78, when elongated (as FIG. 15 shows).

Figure 44:
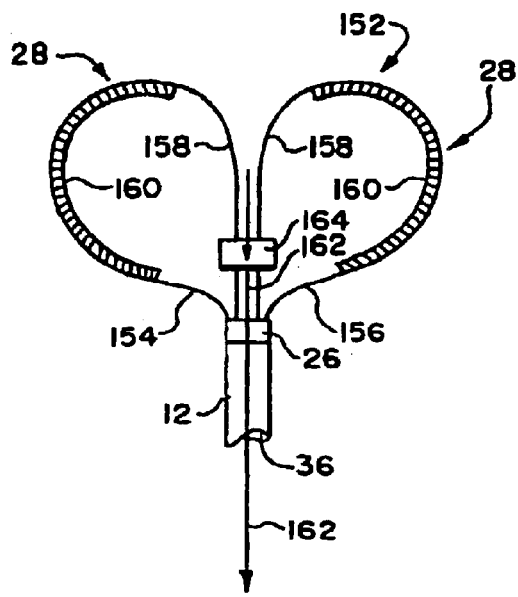
FIGS. 44 and 45 are plan, partially diagrammatic, views of an alternative form of a bifurcated full-loop structure for supporting multiple electrode elements having movable center ring to extend and distend the bifurcated full-loop structure.
Figure 45:
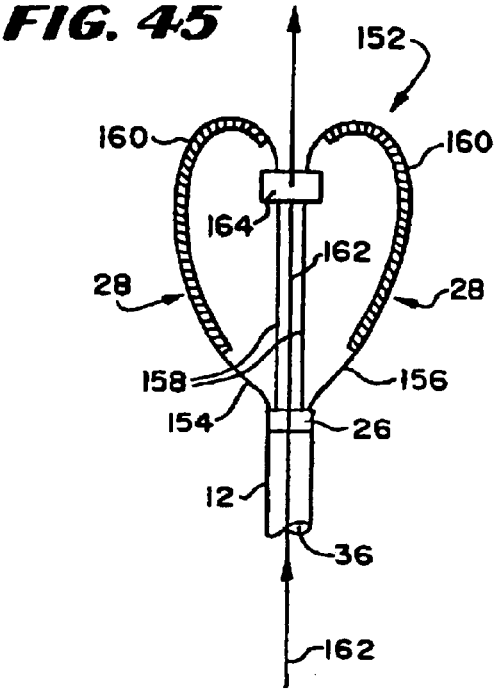

FIGS. 44 and 45 show an alternative embodiment of a bifurcated full-loop structure 152. The structure 152 includes two oppositely spaced spline legs 154/156, each carrying one or more electrode elements 28, like the structure 136 shown in FIGS. 41 to 43. Each spline leg 154/156 is preformed with a resilient memory to assume a desired maximum radius of curvature (which FIG. 44 shows).

Unlike the structure 136 shown in FIGS. 41 to 43, the structure 152 shown in FIGS. 44 and 45 fixes both ends of the spline legs 154/156 to the base 26. The spline legs 154/156 thereby form stationary, side-by-side half-loop structures, each with an inner portion 158 and an outer portion 160. Together, the stationary half-loop structures create the bifurcated full-loop structure 152.

In this arrangement, a center stylet 162 is attached to a ring 164 that commonly encircles the inner portions 158 of the spline legs 154/156 along the center of the structure 152. Movement of the stylet 162 slides the ring 164 along the inner leg portions 158. The stylet 162 passes through the catheter body lumen 36 to a suitable control in the handle (not shown), as already described.

Forward movement of the ring 164 (as FIG. 45 shows) jointly extends the spline legs 154/156, creating a low profile for vascular introduction. Rearward movement of the ring 164 (as FIG. 44 shows) allows the resilient memory of the preformed spline legs 154/156 to bow the legs 154/156 outward into the desired loop shape.

Figure 46:
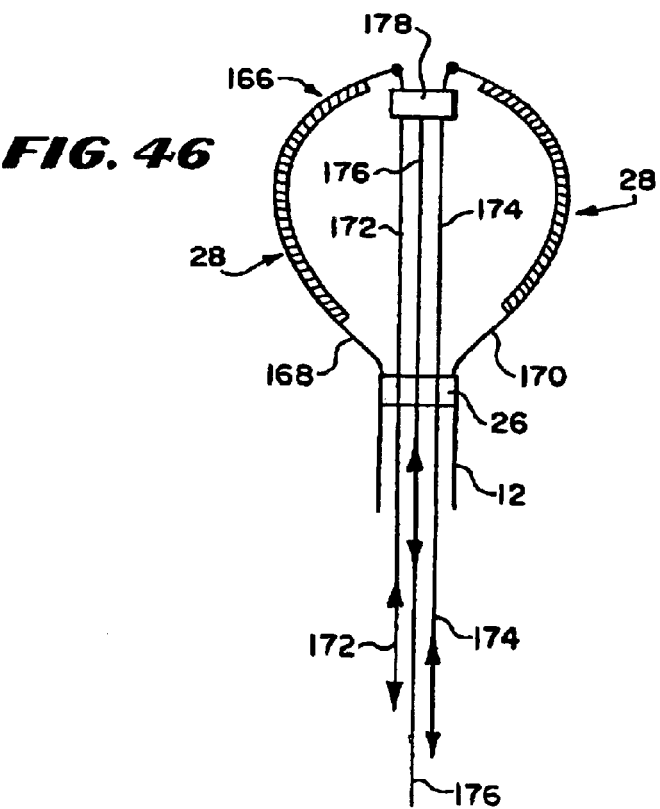
FIG. 46 is a plan, partially diagrammatic, views of an alternative form of a bifurcated full-loop structure for supporting multiple electrode elements having both a movable center ring and movable spline legs to extend and distend the bifurcated full-loop structure.

FIG. 46 shows another alternative embodiment of a bifurcated full-loop structure 166. This structure 166 has two oppositely spaced spline legs 168 and 170, each carrying one or more electrode elements 28. Each spline leg 168/170 is preformed with a resilient memory to assume a maximum radius of curvature (which FIG. 46 shows).

The near end of each spline leg 168/170 is attached to the base 26. The far end of each spline leg 168/170 is individually attached to its own stylet 172/174. Instead of joining a common junction (as in the structure 136 shown in FIGS. 41 to 43), the spline stylets 172/174 of the structure 166 individually pass through the catheter body lumen 36 to suitable control knobs (not shown) in the handle 18. Like the embodiment shown in FIGS. 44 and 45, a third stylet 176 is attached to a ring 178 that encircles the spline stylets 172 and 174. The third stylet 176 passes through the guide tube lumen 36 to its own suitable control knob (not shown) in the handle 18.

The embodiment shown in FIG. 46 allows the physician to move the ring 178 up and down along the spline stylets 172 and 174 to shape and change the flexure of the structure 166 in the manner shown in FIGS. 44 and 45. Independent of this, the physician can also individually move the spline stylets 172 and 174 to further shape and change the flexure of each spline leg 168 and 170, as in the case of the movable spline legs 120/122 shown in FIGS. 36 to 38. This structure 166 thus gives the physician latitude in shaping the loop structure to achieve the desired contact with the atrial wall.

Another alternative embodiment of a bifurcated full-loop structure 180 is shown in FIGS. 47 to 49. In this embodiment, the structure 180 includes two oppositely spaced spline legs 182 and 184, each carrying one or more electrode elements 28. Each spline leg 182/184 is preformed with a resilient memory to assume a desired maximum radius of curvature (which FIG. 49 shows).

The inner portion 186 of each spline leg 182/184 is attached to the base 26. A stationary ring 190 encircles the inner portions 186 near the distal end of the structure 180, holding them together.

The outer portion 188 of each spline leg 182/184 is free of attachment to the base 26 and is resiliently biased away from the base 26. Each outer portion 188 is individually attached to its own stylet 192 and 194. The spline stylets 192 and 194 individually pass through the catheter body lumen 36 to suitable control knobs (not shown) in the handle 18.

Pulling the spline legs stylets 192/194 rearward pulls the outer portion 188 of the attached spline leg 182/184 radially toward the base 26, against their resilient memories, creating a low profile suitable for vascular access (as FIG. 47 shows). Pushing the spline stylets 192/194 forward pushes the outer portion 188 of the attached spline leg 182/184, aided by the resilient memory of the spline leg 182/184, outward (as FIGS. 48 and 49 show). The spline stylets 192/194 can be manipulated together or individually to achieve the shape and flexure desired.

E. Loop Support Structures for Movable Electrodes

FIGS. 50 and 51 show a full-loop structure 196 which supports a movable ablation element 198. The structure 196 includes a pair of spline legs 200 secured at their distal ends to the hub 24 and at their proximal ends to the base 26, in the manner described in association with the structure shown in FIG. 1. A center stiffener 202 extends between the base 26 and the hub 24 to lend further strength.

The ablation element 198 (see FIG. 52) comprises a core body 204 made of an electrically insulating material. The body 204 includes a central lumen 26, through which one of the spline legs 200 passes. The core body 204 slides along the spline leg 200 (as shown by arrows in FIGS. 50 to 52).

In the illustrated and preferred embodiment (see FIG. 52), a coil electrode element 34 (as already described) is wound about the core body 204. Alternatively, the core body 204 can be coated with an electrically conducting material or have an electrically conducting metal band fastened to it. As shown in FIG. 53, the ablation element can also comprise a composite structure 198(1) (see FIG. 53) of two bi-polar electrodes 208 separated by an electrically insulating material 210. The core body 204 of the electrode can range in diameter from 3 Fr to 8 Fr and in length from 3 mm to 10 mm.

A guide wire 212 is attached to at least one end of the ablation electrode 198 (see FIGS. 50 and 52). The guide wire 212 extends from the handle 18 through the catheter body lumen 36, along the center stiffener 202 and through the hub 24 for attachment to the ablation element 198. A signal wire 214 also extends in common along the guide wire 212 (see FIG. 52) to supply ablation energy to the electrode 198. The proximal end of the guide wire 212 is attached to a suitable control knob (not shown) in the handle 18. Movement of the guide wire 212 forward pushes the ablation element 198 along the spline leg 200 from the distal end of the structure 196 to the proximal end.

Two guide wires (212 and 213) may be used (as FIG. 52 shows), which are attached to opposite ends of the ablation element 198. Pulling on one guide wire 212 advances the electrode 198 toward the distal end of the structure 196, while pulling on the other guide wire 213 advances the electrode 198 in the opposite direction toward the proximal end of the structure 196. In an alternative implementation (not shown), the distal tip of a second catheter body can be detachably coupled either magnetically or mechanically to the movable electrode 198. In this implementation, the physician manipulates the distal end of the second catheter body into attachment with the electrode 198, and then uses the second catheter body to drag the electrode 198 along the structure 196.

Figure 54:
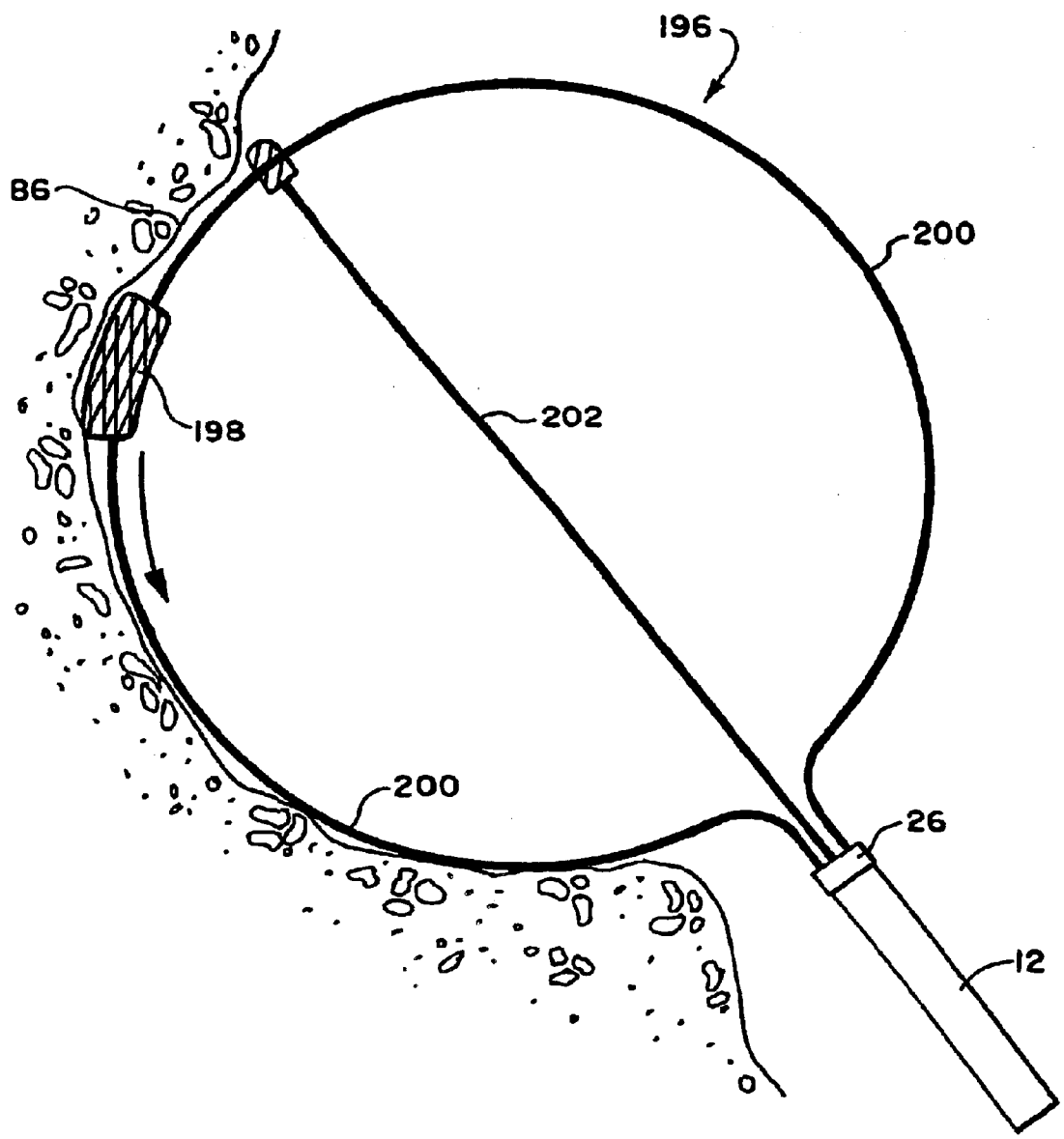
FIG. 54 is a largely diagrammatic view of the full-loop structure and movable electrode element shown in FIG. 50 in use within the atrium of a heart.

In use (as FIG. 54 shows), once satisfactory contact has been established with the atrial wall 86, sliding the ablation electrode 198 along the spline leg 200 while applying ablation energy creates a long and thin lesion pattern. The ablation can be accomplished by either moving the electrode 198 sequentially to closely spaced locations and making a single lesion at each location, or by making one continuous lesion by dragging the electrode 198 along the tissue while ablating.

One or both spline legs 200 can also be movable with respect to the base, as before described, to assure intimate contact between the ablation element 198 and the endocardium.

F. Bundled Loop Structures

The invention makes possible the assembly of bundled, independently adjustable loop structures to form a dynamic three dimensional electrode support structure 228, like that shown in FIGS. 55 to 58.

The structure 228 shown in FIGS. 55 to 58 comprises four spline legs (designated L1, L2, L3, and L4) circumferentially spaced ninety degrees apart. Each spline leg L1, L2, L3, and L4 is generally like that shown in FIG. 29. Each leg L1, L2, L3, and L4 is preformed with resilient memory to assume a curve of selected maximum radius. In the illustrated embodiment, each leg L1 to L4 carries at least one electrode element 28, although one or more of the legs L1 to L4 could be free of electrode elements 28.

The outer portions 230 of each spline leg L1 to L4 are attached to the structure base 26. As FIG. 61 shows, the base 26 is similar to that shown in FIG. 26, having an outer ring 236 and a concentric slotted inner element 238, through which the near ends of the outer spline leg portions 230 extend. The near ends are doubled back upon themselves and wedged in the space 240 between the outer ring 236 and inner element 238, as earlier shown in FIG. 6B.

The inner portions 232 of each spline leg L1, L2, L3, and L4 are not attached to the base 26. They pass through lumens 242 in the inner element 238 of the base 26 (see FIG. 61) and into catheter body lumen 36 for individual attachment to control knobs 234 on the handle 18 (see FIG. 55). Wires 58 associated with the electrode elements 28 carried by each leg L1 to L4 pass through other lumens 244 in the inner element 238 (see FIG. 61).

Figure 55:
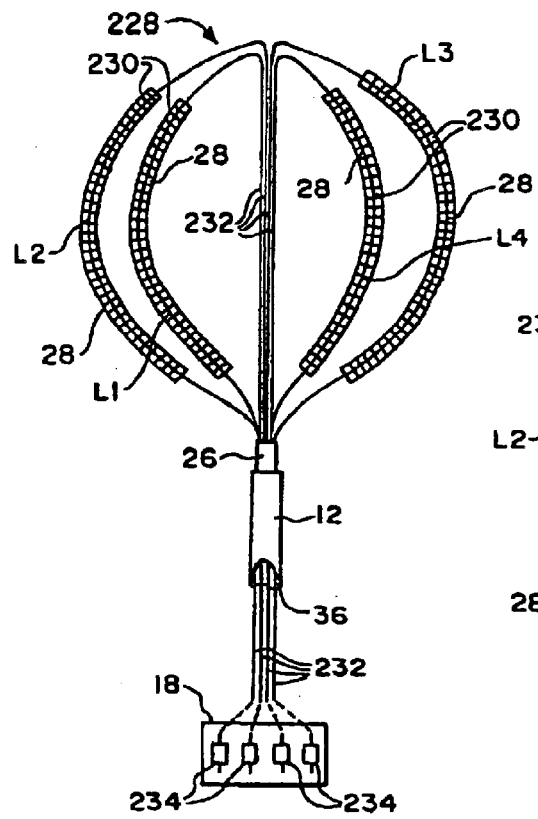
FIG. 55 is a perspective, elevation view of a bundled loop structure for supporting multiple electrode elements, comprising an array of individual spline legs structures, each having a movable portion that independently extends and distends the individual structures to shape and flex the overall bundled loop structure.
Figure 57:
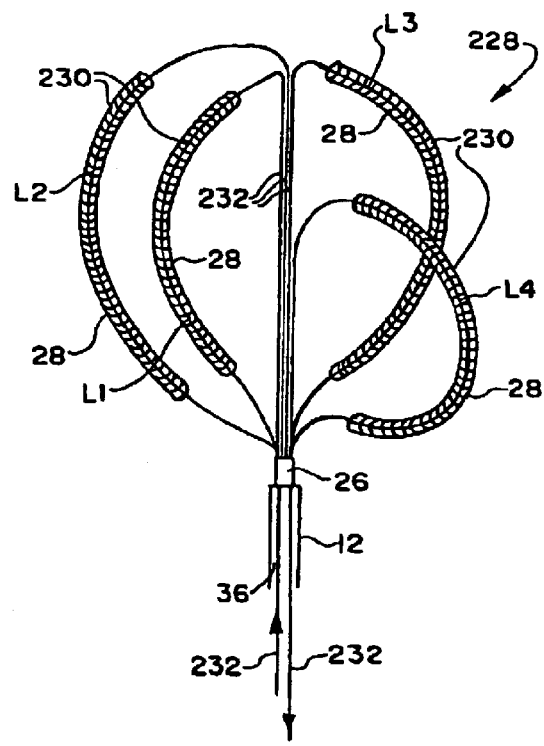
FIG. 57 is a perspective elevation view of the bundled loop structure shown in FIG. 55 with some of the independently movable spline legs extended and distended to change the flexure of the bundled loop structure.
Figure 56:
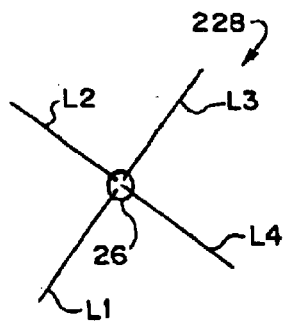
FIG. 56 is a top view of the bundled loop structure shown in FIG. 55.
Figure 58:
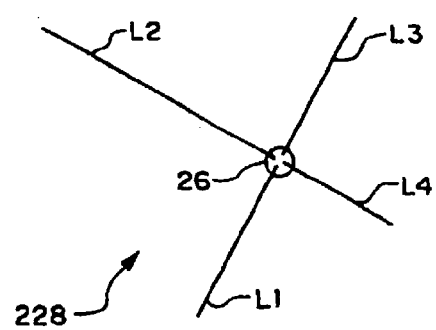
FIG. 58 is a top view of the bundled loop structure shown in FIG. 57.

The inner portion 232 of each spline leg L1 to L4 is independently movable, in the same way as the spline leg shown in FIGS. 31 to 35. By manipulating the control knobs 234, the physician can change the normal flexure of the structure 228 (which FIGS. 55 and 56 show) to a new flexure (which FIGS. 57 and 58 show), by altering the shape each spline leg L1 to L4 independent of each other. As FIGS. 57 and 58 show, the inner portion 232 of leg L4 has been pulled aft, compressing the associated loop. The inner portion 232 of leg L2 has been pushed forward, expanding the associated loop.

As FIGS. 59A/B and 60A/B show, by selective manipulation of the movable inner portions 232 of the spline legs L1 to L4, the physician can adjust the shape of the three dimensional loop structure 228 within the atrium 88 from one that fails to make sufficient surface contact between the electrode element 28 and the atrial wall 86 (as FIGS. 59A/B show) to one that expands the atrium 88 and creates an extended region of surface contact with the atrial wall 86 (as FIGS. 60A/60B show). The physician can thereby tailor the shape of the three dimensional structure 228 to the particular physiology of the patient.

In an alternative arrangement, the inner portions 232 of the spline legs L1 to L4 can be fixed to the base 26 and the outer portions 230 made free to move in the manner shown in FIGS. 47 to 49.

III. Conclusion

It should be now be apparent that one or more movable spline legs can be used in association with a movable center stylet to provide control of the shape and flexure of the ablation element. The further inclusion of steering wires on the movable stylet, or the use of a malleable stylet and/or malleable spline legs adds the ability to form curvilinear lesion patterns.

It is thereby possible to combine in a single loop support structure one or more movable spline legs (as FIGS. 31 to 38 show), a movable center stylet (as FIGS. 13 to 19 show), and a stylet steering assembly or malleable stylet/splines (as FIGS. 20 to 28 show). Such a structure is capable of creating a diverse number of shapes and contact forces to reliably achieve the type and degree of contact desired between the ablation elements and the targeted tissue area, despite physiologic differences among patients.

It should also be appreciated that the invention is applicable for use in tissue ablation applications that are not catheter-based. For example, any of the loop structures like those described in this application can be mounted at the end of hand-held probe for direct placement by the physician in contact with a targeted tissue area. For example, a hand held loop structure carrying multiple electrodes can be manipulated by a physician to ablate tissue during open heart surgery for mitral valve replacement.

Various features of the invention are set forth in the following claims.

We claim:

1. An apparatus, comprising:
   a guide body defining a distal end;
   a flexible member associated with the distal end of the guide body;
   an energy transmission device carried by the flexible member; and
   a malleable stylet extending outwardly from the distal end of the guide body and secured to the flexible member.

2. An apparatus as claimed in claim 1, wherein the malleable stylet is configured such that it may be bent into a bent orientation in response to an external force without bending the guide body and will remain in the bent orientation when the external force is removed.

3. An apparatus as claimed in claim 1, wherein
   the malleable stylet defines an axis; and
   the flexible member is bent in a first direction that extends along and radially outward of the stylet axis.

4. An apparatus as claimed in claim 1, wherein
   the flexible member defines a distal end; and
   the stylet is secured to the distal end of the flexible member.

5. An apparatus as claimed in claim 1, wherein
   the flexible member defines a loop having a distal region; and
   the stylet is secured to the distal region of the loop.

6. An apparatus as claimed in claim 5, wherein the flexible member comprises first and second splines.

7. An apparatus as claimed in claim 1, wherein the energy transmission device comprises an electrode.

8. An apparatus as claimed in claim 1, wherein the energy transmission device comprises a flexible electrode.

9. An apparatus as claimed in claim 1, further comprising:
   a control element adapted to move the stylet relative to the flexible member.

10. An apparatus as claimed in claim 1, wherein the flexible member comprises a spline.

11. An apparatus, comprising:
    a guide body defining a distal end;
    a malleable support member associated with the distal end of the guide body;
    an energy transmission device carried by the malleable support member; and
    a longitudinally movable stylet extending outwardly from the distal end of the guide body and secured to the malleable support member.

12. An apparatus as claimed in claim 11, wherein the malleable support member is configured such that it may be bent into a bent orientation in response to an external force without bending the guide body and will remain in the bent orientation when the external force is removed.

13. An apparatus as claimed in claim 11, wherein the stylet is malleable.

14. An apparatus as claimed in claim 13, wherein the malleable stylet is configured such that it may be bent into a bent orientation in response to an external force without bending the guide body and will remain in the bent orientation when the external force is removed.

15. An apparatus as claimed in claim 11, wherein the malleable support member defines a distal end; and the stylet is secured to the distal end of the support member.

16. An apparatus as claimed in claim 11, wherein the malleable support member defines a loop having a distal region; and the stylet is secured to the distal region of the loop.

17. An apparatus as claimed in claim 16, wherein the malleable support member comprises first and second malleable splines.

18. An apparatus as claimed in claim 11, wherein the energy transmission device comprises an electrode.

19. An apparatus as claimed in claim 11, wherein the energy transmission device comprises a flexible electrode.

20. An apparatus as claimed in claim 11, further comprising:

a control element adapted to move the stylet relative to the malleable support member.

21. An apparatus, comprising:

a guide body defining a distal end;

a support member associated with the distal end of the guide body;

an energy transmission device carried by the support member; and a stylet extending outwardly from the distal end of the guide body and secured to the support member;

wherein at least one of the support member and the stylet is malleable.

22. An apparatus as claimed in claim 21, wherein the at least one of the support member and the stylet is configured such that it may be bent into a bent orientation in response to an external force without bending the guide body and will remain in the bent orientation when the external force is removed.

23. An apparatus as claimed in claim 21, wherein the support member defines a distal end; and the stylet is secured to the distal end of the support member.

24. An apparatus as claimed in claim 21, wherein the support member defines a loop having a distal region; and the stylet is secured to the distal region of the loop.

25. An apparatus as claimed in claim 24, wherein the support member comprises first and second splines.

26. An apparatus as claimed in claim 21, wherein the energy transmission device comprises an electrode.

27. An apparatus as claimed in claim 21, wherein the energy transmission device comprises a flexible electrode.

28. An apparatus as claimed in claim 21, further comprising:

a control element adapted to move the stylet relative to the support member.

\* \* \* \* \*